(12) United States Patent
Dong

(10) Patent No.: US 9,074,014 B2
(45) Date of Patent: Jul. 7, 2015

(54) ANALOGUES OF GLUCOSE-DEPENDENT INSULINOTROPIC POLYPEPTIDE

(75) Inventor: Zheng Xin Dong, Holliston, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 891 days.

(21) Appl. No.: 13/057,760

(22) PCT Filed: Aug. 7, 2009

(86) PCT No.: PCT/US2009/004552
§ 371 (c)(1),
(2), (4) Date: Feb. 5, 2011

(87) PCT Pub. No.: WO2010/016940
PCT Pub. Date: Feb. 11, 2010

(65) Prior Publication Data
US 2011/0136733 A1     Jun. 9, 2011

Related U.S. Application Data

(60) Provisional application No. 61/200,629, filed on Dec. 2, 2008, provisional application No. 61/188,191, filed on Aug. 7, 2008.

(51) Int. Cl.
*A61K 38/00*     (2006.01)
*C07K 14/605*    (2006.01)

(52) U.S. Cl.
CPC ............... *C07K 14/605* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,450,266 B2 | 5/2013 | Dong et al. | |
| 2003/0232761 A1 | 12/2003 | Hinke et al. | |
| 2005/0277590 A1 | 12/2005 | O'Harte et al. | |
| 2006/0293232 A1 | 12/2006 | Levy et al. | |
| 2007/0042952 A1 | 2/2007 | Dong et al. | |
| 2007/0167370 A1* | 7/2007 | Gault et al. ..................... | 514/12 |
| 2008/0009603 A1 | 1/2008 | Gault et al. | |
| 2008/0051557 A1 | 2/2008 | Bachovchin et al. | |
| 2008/0124347 A1 | 5/2008 | Kim et al. | |
| 2008/0139459 A1 | 6/2008 | Bos et al. | |
| 2008/0182795 A1 | 7/2008 | Wolfe et al. | |
| 2011/0136725 A1 | 6/2011 | Dong | |
| 2011/0144007 A1 | 6/2011 | Dong | |

FOREIGN PATENT DOCUMENTS

| | | |
|---|---|---|
| EP | 0479210 B1 | 5/1995 |
| EP | 1069137 A1 | 1/2001 |
| EP | 1942115 A1 | 7/2008 |
| WO | 02/082047 A2 | 10/2002 |
| WO | 03/011115 A2 | 2/2003 |
| WO | 2004103390 A2 | 12/2004 |
| WO | WO 2005/082928 | 9/2005 |
| WO | 2006086769 A2 | 8/2006 |
| WO | 2006121904 A1 | 11/2006 |
| WO | 2007/028632 A2 | 3/2007 |
| WO | WO 2007/028633 | 3/2007 |
| WO | WO 2007028633 A2 * | 3/2007 |
| WO | 2007/049695 A1 | 5/2007 |
| WO | WO 2008/021560 | 2/2008 |

OTHER PUBLICATIONS

Salhanick et al., "Contribution of site-specific PEGylation to the dipeptidyl peptidase IV stability of glucose-dependent insulinotropic polypeptide," Bioorg. & Med. Chem. Lett. 15:4114-4117 (2005).*
Gault, Victor A. et al. "Glucose-dependent insulinotropic polypeptide analogues and their therapeutic potential for the treatment of obesity-diabetes," Biochemical and Biophysical Research Communications, 2003, p. 207-213, vol. 308, No. 2.
Gault, Victor A. et al. "Improved biological activity of Gly2- and Ser2-substituted analogues of glucose-dependent insulinotrophic polypeptide," Journal of Endocrinology, 2003, p. 133-141, vol. 176, No. 1.
Green, Brian D. "Structurally Modified Analogues of Glucagon-Like Peptide-1 (GLP-1) and Glucose-Dependent Insulinotropic Polypeptide (GIP) as Future Antidiabetic Agents," Current Pharmaceutical Design, 2004, p. 3651-3662, vol. 10, No. 29.
Irwin, Nigel et al. "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biological Chemistry, 2005, p. 679-687, vol. 386, No. 7.
Irwin, Nigel et al. "GIP(Lys16PAL) and GIP(Lys37PAL): Novel Long-Acting Acylated Analogues of Glucose-Dependent Insulinotropic Polypeptide with Improved Antidiabetic Potential," Journal of Medicinal Chemistry, 2006, p. 1047-1054, vol. 49, No. 3.
O'Harte, F. P. M., et al., "Gastric inhibitory polypeptide and effects of glycation on glucose transport and metabolism in isolated mouse abdominal muscle", J. Endocrinology, 1998, 156:237-243.
Gault, V.A. et al., "DPP IV resistance and insulin releasing activity of a novel di-substituted analogue of glucose-dependent insulinotropic polypeptide, (Ser2-Asp13)GIP," Cell Biology Int'l, 2003, vol. 27, p. 41-46.
Gault, V.A. et al., "C-terminal mini-PEGylation of glucose-dependent insulinotropic polypeptide exhibits metabolic stability and improved glucose homeostasis in dietary-induced diabetes," Biochem. Pharma., 2008, vol. 75, p. 2325.
Irwin, N. et al., "Degradation, Insulin Secretion, and Antihyperglycemic Actions of Two Palmitate-Derivitized N-Terminal Pyroglutamyl Analogues of Glucose-Dependent Insulinotropic Polypeptide," J. Med. Chem., 2005, vol. 48, p. 1244.
Irwin, N. et al., "Evaluation of the antidiabetic activity of DPP IV resistant N-terminally modified versus mid-chain acylated analogues of glucose-dependent insulinotropic polypeptide," Biochem. Pharma., 2006, vol. 72, p. 719.
O'Harte, F.P.M., et al., "Antagonistic effects of two novel GIP analogs, (Hyp3)GIP and (Hyp3)GIPLys16PAL, on the biological actions of GIP and longer-term effects in diabetic ob/ob mice," Am. J. Physiol. Endocrinol. Metab., 2007, vol. 292, p. E1674.

* cited by examiner

*Primary Examiner* — Julie Ha
*Assistant Examiner* — Kristina M Hellman
(74) *Attorney, Agent, or Firm* — Ipsen Bioscience Inc.; Janice M. Klunder; Eileen J. Ennis

(57) ABSTRACT

A series of glucose-dependent insulinotropic polypeptide analog compounds, pharmaceutical compositions, and the use of the GIP polypeptide analog compounds as GIP-receptor agonists or antagonists for the treatment of GIP-receptor mediated conditions, such as non-insulin dependent diabetes mellitus and obesity.

16 Claims, No Drawings

ANALOGUES OF GLUCOSE-DEPENDENT INSULINOTROPIC POLYPEPTIDE

This application is a United States national stage filing under 35 U.S.C. §371 of international (PCT) application no. PCT/US2009/004552, filed Aug. 7, 2009, and designating the US, which claims priority to U.S. provisional application nos. 61/188,191, filed Aug. 7, 2008, and 61/200,629, filed Dec. 2, 2008.

FIELD OF THE INVENTION

The present invention relates to the area of novel analogues of glucose-dependent insulinotropic polypeptide compounds, pharmaceutical compositions containing said compounds, and the use of said compounds as GIP-receptor agonists or antagonists for treatment of GIP-receptor mediated conditions, such as non-insulin dependent diabetes mellitus and obesity.

BACKGROUND ART

Glucose-dependent insulinotropic polypeptide ("GIP", also known as "gastric inhibitory polypeptide"; SEQ ID NO:1) is a 42-residue peptide secreted by enteroendorine K-cells of the small intestine into the bloodstream in response to oral nutrient ingestion. GIP inhibits the secretion of gastric acid, and it has been shown to be a potent stimulant for the secretion of insulin from pancreatic beta cells after oral glucose ingestion (the "incretin effect") (Creutzfeldt, W., et al., 1979, *Diabetologia*, 16:75-85).

Insulin release induced by the ingestion of glucose and other nutrients is due to both hormonal and neural factors (Creutzfeldt, W., et al., 1985, *Diabetologia*, 28:565-573). Several gastrointestinal regulatory peptides have been proposed as incretins, and among these candidates, only GIP and glucagon-like peptide 1 ("GLP-1") appear to fulfill the requirements to be considered physiological stimulants of postprandial insulin release (Nauck, et al., 1989, *J. Clin. Endorinol. Metab.*, 69:654-662). It has been shown that the combined effects of GIP and GLP-1 are sufficient to explain the full incretin effect of the enteroinsular axis (Fehmann, H. C., et al., 1989, *FEBS Lett.*, 252:109-112).

As is well known to those skilled in the art, the known and potential uses of GIP are varied and multitudinous. Thus, the administration of the compounds of this invention for purposes of eliciting an agonist effect can have the same effects and uses as GIP itself. These varied uses of GIP may be summarized as follows: treating a disease selected from the group consisting of type 1 diabetes, type 2 diabetes (Visboll, T., 2004, *Dan. Med. Bull.*, 51:364-70), insulin resistance (WO 2005/082928), obesity (Green, B. D., et al., 2004, *Current Pharmaceutical Design*, 10:3651-3662), metabolic disorder (Gault, V. A., et al., 2003, *Biochem. Biophys. Res. Commun.*, 308:207-213), central nervous system disease, neurodegenerative disease, congestive heart failure, hypoglycemia, and disorders wherein the reduction of food intake and weight loss are desired. In pancreatic islets, GIP not only enhances insulin secretion acutely, but it also stimulates insulin production through enhancement of proinsulin transcription and translation (Wang, et al., 1996, *Mol. Cell. Endocrinol.*, 116:81-87) and enhances the growth and survival of pancreatic beta cells (Trumper, et al., 2003, *Diabetes*, 52:741-750). In addition to effects on the pancreas to enhance insulin secretion, GIP also has effects on insulin target tissues directly to lower plasma glucose: enhancement of glucose uptake in adipose (Eckel, et al., 1979, *Diabetes*, 28:1141-1142) and muscle (O'Harte, et al., 1998, *J. Endocrinol.*, 156:237-243), and inhibition of hepatic glucose production (Elahi, D., et al., 1986, *Can. J. Physiol. Pharmacol.*, 65:A18).

In addition, a GIP receptor antagonist in accordance with the present invention inhibits, blocks or reduces glucose absorption from the intestine of an animal. In accordance with this observation, therapeutic compositions containing GIP antagonists may be used in patients with non-insulin dependent diabetes mellitus to improve tolerance to oral glucose in mammals, such as humans, to prevent, inhibit or reduce obesity by inhibiting, blocking or reducing glucose absorption from the intestine of the mammal.

The use of unmodified GIP as a therapeutic, however, is limited by the short in vivo half-life of about 2 minutes (Said and Mutt, 1970, *Science*, 169:1217-1218). In serum, both incretins, GIP and GLP-1, are degraded by dipeptidyl peptidase IV ("DPPIV"). Improving the stability of GIP to proteolysis not only maintains the activity of GIP at its receptor but, more importantly, prevents the production of GIP fragments, some of which act as GIP receptor antagonists (Gault, et al., 2002, *J. Endocrinol.*, 175:525-533). Reported modifications have included protection of the N-terminus of GIP from proteolysis by DPPIV through modification of the N-terminal tyrosine (O'Harte, et al., 2002, *Diabetologia*, 45:1281-1291), mutation of the alanine at position 2 (Hinke, et al., 2002, *Diabetes*, 51:656-661), mutation of glutamic acid at position 3 (Gault, et al., 2003, *Biochem. Biophys. Res. Commun.*, 308:207-213), and mutation of alanine at position 13 (Gault, et al., 2003, *Cell Biol. International*, 27:41-46), The following patent applications have been filed related to the effects of GIP analogues on the function of various target organs and their potential use as therapeutic agents:

PCT publication WO 00/58360 discloses peptidyl analogues of GIP which stimulate the release of insulin. In particular, this application discloses specific peptidyl analogues comprising at least 15 amino acid residues from the N-terminal end of GIP(1-42), e.g., an analogue of GIP containing exactly one amino acid substitution or modification at positions 1, 2 and 3, such as [Pro$^3$]GIP(1-42).

PCT publication WO 98/24464 discloses an antagonist of GIP consisting essentially of a 24-amino acid polypeptide corresponding to positions 7-30 of the sequence of GIP, a method of treating non-insulin dependent diabetes mellitus and a method of improving glucose tolerance in a non-insulin dependent diabetes mellitus patient.

PCT publication WO 03/082898 discloses C-terminal truncated fragments and N-terminal modified analogues of GIP, as well as various GIP analogues with a reduced peptide bond or alterations of the amino acids close to the DPPIV-specific cleavage site. This application further discloses analogues with different linkers between potential receptor binding sites of GIP. The compounds of this application are alleged to be useful in treating GIP-receptor mediated conditions, such as non-insulin dependent diabetes mellitus and obesity.

There exists a need for improved analogues of GIP, which are stable in formulation and have long plasma half-life in vivo resulting from decreased susceptibility to proteolysis and decreased clearance while maintaining binding affinity to a GIP receptor to elicit respective agonistic or antagonistic effects. Moreover, among other therapeutic effects of the compounds of the present invention as illustrated herein, tighter control of plasma glucose levels may prevent long-term diabetic complications, thereby providing an improved quality of life for patients.

SUMMARY OF THE INVENTION

In one aspect, the invention relates to peptide variants of GIP of the following formula (I):

$(R^2R^3)$-$A^1$-$A^2$-$A^3$-$A^4$-$A^5$-$A^6$-$A^7$-$A^8$-$A^9$-$A^{10}$-$A^{11}$-$A^{12}$-
$A^{13}$-$A^{14}$-$A^{15}$-$A^{16}$-$A^{17}$-$A^{18}$-$A^{19}$-$A^{20}$-$A^{21}$-$A^{22}$-
$A^{23}$-$A^{24}$-$A^{25}$-$A^{26}$-$A^{27}$-$A^{28}$-$A^{29}$-$A^{30}$-$A^{31}$-$A^{32}$-
$A^{33}$-$A^{34}$-$A^{35}$-$A^{36}$-$A^{37}$-$A^{38}$-$A^{39}$-$A^{40}$-$A^{41}$-$A^{42}$-
$A^{43}$-$R^1$, (I)

wherein:

$A^1$ is Tyr, N-Me-Tyr, 4Hppa, Orn(N—C(O)—(CH$_2$)$_{12}$—CH$_3$) or HN—CH((CH$_2$)$_n$—N(R$^4$R$^5$))—C(O);

$A^2$ is Ala, Abu, D-Abu, Acc, Aib, β-Ala, D-Ala, Gaba, Gly, Ser, D-Ser, Thr, D-Thr, Val, or D-Val;

$A^3$ is Glu, Aib, Asp, NMe-Asp, Dhp, Dmt, Glu, NMe-Glu, 3Hyp, 4Hyp, 4Ktp, Pro, hPro, Thz, or Tic;

$A^4$ is Gly, Acc, Aib, or β-Ala;

$A^5$ is Thr, Acc, Aib, or Ser;

$A^6$ is Phe, Acc, Aib, Aic, Cha, 1Nal, 2Nal, 2-Pal, 3-Pal, 4-Pal, (X$^4$,X$^5$,X$^6$,X$^7$,X$^8$)Phe, or Trp;

$A^7$ is Ile, Abu, Acc, Aib, Ala, Cha, Leu, Nle, Phe, Tle, or Val;

$A^8$ is Ser, Aib, or Thr;

$A^9$ is Asp, Aib, or Glu;

$A^{10}$ is Tyr, Acc, Cha, 1Nal, 2Nal, 2-Pal, 3-Pal, 4-Pal, Phe, or (X$^4$,X$^5$,X$^6$,X$^7$,X$^8$)Phe;

$A^{11}$ is Ser, Acc, Aib, Nle, or Thr;

$A^{12}$ is Ile, Abu, Acc, Aib, Ala, Cha, Leu, Nle, Phe, Tle, or Val;

$A^{13}$ is Ala, Acc, Aib, β-Ala, D-Ala, Gly, or Ser;

$A^{14}$ is Met, Abu, Acc, Aib, Ala, Cha, Ile, Leu, Nle, Phe, Tle, or Val;

$A^{15}$ is Asp, Aib, or Glu;

$A^{16}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), or Pen(succinimide-N—(CH$_2$)$_s$—NH—C(O)—(CH$_2$)$_t$—CH$_3$);

$A^{17}$ is Ile, Abu, Acc, Aib, Ala, Cha, Leu, Nle, Phe, Tle, or Val;

$A^{18}$ is His, Amp, Arg, 2-Pal, 3-Pal, 4-Pal, Phe, or Tyr;

$A^{19}$ is Gln, Aib, or Asn;

$A^{20}$ is Gln, Aib, or Asn;

$A^{21}$ is Asp, Aib, or Glu;

$A^{22}$ is Phe, Acc, Aib, Aic, Cha, 1Nal, 2Nal, 2-Pal, 3-Pal, 4-Pal, (X$^4$,X$^5$,X$^6$,X$^7$,X$^8$)Phe, or Trp;

$A^{23}$ is Val, Abu, Acc, Aib, Ala, Cha, Ile, Leu, Nle, or Tle;

$A^{24}$ is Asn, Aib, or Gln;

$A^{25}$ is Trp, Acc, Aib, 1Nal, 2Nal, 2-Pal, 3-Pal, 4-Pal, Phe, or (X$^4$,X$^5$,X$^6$,X$^7$,X$^8$)Phe;

$A^{26}$ is Leu, Acc, Aib, Cha, Ile, Nle, Phe, (X$^4$,X$^5$,X$^6$,X$^7$,X$^8$)Phe, or Tle;

$A^{27}$ is Leu, Acc, Aib, Cha, Ile, Nle, Phe, (X$^4$,X$^5$,X$^6$,X$^7$,X$^8$)Phe, or Tle;

$A^{28}$ is Ala, Acc, or Aib;

$A^{29}$ is Gln, Aib, Asn, or deleted;

$A^{30}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{31}$ is Gly, Acc, Aib, β-Ala, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), His, Pen(succinimide-N—(CH$_2$)$_s$—NH—C(O)—(CH$_2$)$_t$—CH$_3$), or deleted;

$A^{32}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{33}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{34}$ is Asn, Aib, Gln, Ser, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{35}$ is Asp, Aib, Glu, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{36}$ is Trp, Acc, Aib, 1Nal, 2Nal, 2-Pal, 3-Pal, 4-Pal, Phe, (X$^4$,X$^5$,X$^6$,X$^7$,X$^8$)Phe, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

$A^{37}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C (O)—(CH$_2$)$_t$—CH$_3$), Pen(succinimide-N—(CH$_2$)$_s$—NH—C(O)—(CH$_2$)$_t$—CH$_3$), or deleted;

A$^{38}$ is His, Amp, 2-Pal, 3-Pal, 4-Pal, Phe, Tyr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{39}$ is Asn, Aib, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{40}$ is Ile, Acc, Aib, Ser, Thr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{41}$ is Thr, Acc, Aib, Asn, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{42}$ is Gln, Acc, Aib, Asn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{43}$ is Acc, Aib, Ala, Asp, Gln, His, Phe, Thr, Trp, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

R$^1$ is OH, NH$_2$, (C$_1$-C$_{30}$)alkoxy, or NH—X$^2$—CH$_2$—Z$^0$, wherein X$^2$ is a (C$_0$-C$_{30}$) hydrocarbon moiety and Z$^0$ is H, OH, CO$_2$H, or CONH$_2$;

each of R$^2$, R$^3$, R$^4$ and R$^5$ is independently selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl; provided that when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl; further provided that when R$^4$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^5$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl (C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;

n is, independently for each occurrence, an integer from 1 to 5 inclusive;

s, t, x and y each is, independently for each occurrence, an integer from 1 to 30 inclusive;

X$^4$, X$^5$, X$^6$, X$^2$ and X$^8$ each is, independently for each occurrence, H, F, Cl, Br, I, (C$_{1-10}$)alkyl, substituted (C$_{1-10}$)alkyl, aryl, substituted aryl, OH, NH$_2$, NO$_2$, or CN;

provided that when A$^1$ is 4Hppa, then R$^2$ and R$^3$ are deleted;

further provided that only one amino acid at positions 1, 2 or 3 of the compound is substituted or modified; and further provided that the compound of formula (I) is not (D-Ala$^2$)hGIP(1-42), (Pro$^3$)hGIP(1-42) (SEQ ID NO:120), (Aib$^3$)hGIP(1-42) (SEQ ID NO:121), (Ser$^2$)hGIP(1-42) (SEQ ID NO:122), (Abu$^2$)hGIP(1-42) (SEQ ID NO: 123), (D-Abu$^2$)hGIP(1-42), (D-Ser$^2$)hGIP(1-42), (D-Thr$^2$)hGIP(1-42), or (D-Val$^2$)hGIP(1-42).

A subset (A) of the compounds covered by the above formula (I) are those in which:

A$^1$ is Tyr, N-Me-Tyr, 4Hppa, or Orn(N—C(O)—(CH$_2$)$_{12}$—CH$_3$);
A$^2$ is Ala, A5c, A6c, Aib, D-Ala, Gly, or Ser;
A$^3$ is Glu, Dhp, 3Hyp, 4Hyp, Pro, hPro, or Tic;
A$^4$ is Gly or Aib;
A$^5$ is Thr, A5c, or Aib;
A$^6$ is Phe or A6c;
A$^7$ is Ile, A5c, A6c, or Aib;
A$^8$ is Ser or Aib;
A$^9$ is Asp or Aib;
A$^{10}$ is Tyr;
A$^{11}$ is Ser, A5c, A6c, Aib, or Nle;
A$^{12}$ is Ile, A5c, or Aib;
A$^{13}$ is Ala or Aib;
A$^{14}$ is Met, A5c, A6c, or Nle;
A$^{15}$ is Asp;
A$^{16}$ is Lys;
A$^{17}$ is Ile or A6c;
A$^{18}$ is His;
A$^{19}$ is Gln;
A$^{20}$ is Gln;
A$^{21}$ is Asp;
A$^{22}$ is Phe;
A$^{23}$ is Val;
A$^{24}$ is Asn;
A$^{25}$ is Trp;
A$^{26}$ is Leu or A6c;
A$^{27}$ is Leu or A6c;
A$^{28}$ is Ala or Aib;
A$^{29}$ is Gln;
A$^{30}$ is Lys;

$A^{31}$ is Gly, Aib, Cys(Psu), His, or deleted;
$A^{32}$ is Lys, Cys(Psu), or deleted;
$A^{33}$ is Lys, Cys(Psu), or deleted;
$A^{34}$ is Asn, Cys(Psu), or deleted;
$A^{35}$ is Asp, Cys(Psu), or deleted;
$A^{36}$ is Trp, Cys(Psu), or deleted;
$A^{37}$ is Lys, Cys(Psu), or deleted;
$A^{38}$ is His, Cys(Psu), or deleted;
$A^{39}$ is Asn, Cys(Psu), or deleted;
$A^{40}$ is Ile, A5c, A6c, Cys(Psu), or deleted;
$A^{41}$ is Thr, A5c, A6c, Aib, Cys(Psu), or deleted;
$A^{42}$ is Gln or deleted;
$A^{43}$ is Cys(Psu), Gln, His, or deleted; and
provided that the compound contains at least one additional amino acid substitution or modification at positions 4-43.

A subset of the compounds of the preceding subset (A) are those in which $A^2$ is D-Ala.

Another subset of the compounds of the preceding subset (A) are those in which $A^{31}$ to $A^{43}$ are deleted.

Another subset of the compounds of the preceding subset (A) are those in which $A^2$ is Ala, A5c, A6c, or Gly; and $A^3$ is Glu, Dhp, 3Hyp, 4Hyp, hPro, or Tic.

Another aspect of the present invention encompasses compounds consisting essentially of a sequence of the first 30 consecutive amino acid residues from the N-terminal end of the native hGIP amino acid sequence, wherein the sequence comprises A5c, A6c, Aib, D-Ala, Gly or Ser substitution at position 2, and at least one additional amino acid substitution or modification at positions 3-30.

A subset of the compounds of the immediately preceding aspect of the present invention are those in which $A^2$ is Aib; $A^3$ is Pro; and at least one of $A^7$, $A^{11}$, $A^{13}$ and $A^{14}$ is not the amino acid residue of the corresponding position in the native GIP.

Yet another aspect of the present invention encompasses GIP analogues comprising A5c, A6c, Aib, D-Ala, Gly or Ser substitution at position 2, and at least one additional amino acid substitution or modification at positions 1 and 3-42.

A subset of the compounds of the immediately preceding aspect of the present invention are those in which $A^2$ is Aib.

Preferred compounds of formula (I) are:
Example 1: (Aib$^{2, 11}$)hGIP(1-42)-OH (SEQ ID NO:4);
Example 2: (Aib$^{2, 9}$)hGIP(1-42)-OH (SEQ ID NO:5);
Example 3: (Aib$^{2, 7}$)hGIP(1-42)-OH (SEQ ID NO:6);
Example 4: (Aib$^{2, 5}$)hGIP(1-42)-OH (SEQ ID NO:7);
Example 5: (Aib$^2$, A5c$^5$)hGIP(1-42)-OH (SEQ ID NO:8);
Example 6: (Aib$^2$, A5c$^7$)hGIP(1-42)-OH (SEQ ID NO:9);
Example 7: (Aib$^2$, A5c$^{12}$)hGIP(1-42)-OH (SEQ ID NO:10);
Example 8: (Aib$^{2, 12}$)hGIP(1-42)-OH (SEQ ID NO:11);
Example 9: (Aib$^{2, 8}$)hGIP(1-42)-OH (SEQ ID NO:12);
Example 10: (Aib$^{2, 4}$)hGIP(1-42)-OH (SEQ ID NO:13);
Example 11: (Aib$^2$, A5c$^5$)hGIP(1-30)-NH$_2$ (SEQ ID NO:14);
Example 12: (Aib$^2$, A5c$^7$)hGIP(1-30)-NH$_2$ (SEQ ID NO:15);
Example 13: (Aib$^2$, A5c$^{12}$)hGIP(1-30)-NH$_2$ (SEQ ID NO:16);
Example 14: (Aib$^{2, 4}$)hGIP(1-30)-NH$_2$ (SEQ ID NO:17);
Example 15: (Aib$^{2, 5}$)hGIP(1-30)-NH$_2$ (SEQ ID NO:18);
Example 16: (Aib$^{2, 7}$)hGIP(1-30)-NH$_2$ (SEQ ID NO:19);
Example 17: (Aib$^{2, 8}$)hGIP(1-30)-NH$_2$ (SEQ ID NO:20);
Example 18: (Aib$^{2, 9}$)hGIP(1-30)-NH$_2$ (SEQ ID NO:21);
Example 19: (Aib$^{2, 11}$)hGIP(1-30)-NH$_2$ (SEQ ID NO:22);
Example 20: (Aib$^{2, 12}$)hGIP(1-30)-NH$_2$ (SEQ ID NO:23);
Example 21: (Aib$^{2, 13}$, A6c$^7$, Nle$^{14}$)hGIP(1-42)-OH (SEQ ID NO:24);
Example 22: (Aib$^{2, 31}$, A6c$^7$)hGIP(1-42)-OH (SEQ ED NO:25);
Example 23: (Aib$^{2, 41}$, A6c$^7$)hGIP(1-42)-OH (SEQ ID NO:26);
Example 24: (Aib$^{2, 31}$, A6c$^7$, Nle$^{14}$)hGIP(1-42)-OH (SEQ ID NO:27);
Example 25: (Aib$^{2, 41}$, A6c$^7$, Nle$^{14}$)hGIP(1-42)-OH (SEQ ID NO:28);
Example 26: (Aib$^2$, A6c$^{7, 26}$, Nle$^{14}$)hGIP(1-42)-OH (SEQ ID NO:29);
Example 27: (Aib$^2$, A6c$^{7, 27}$, Nle$^{14}$)hGIP(1-42)-OH (SEQ ID NO:30);
Example 28: (Aib$^2$, A6c$^{7, 40}$, Nle$^{14}$)hGIP(1-42)-OH (SEQ ID NO:31);
Example 29: (Aib$^2$, A6c$^{7, 41}$, Nle$^{14}$)hGIP(1-42)-OH (SEQ ID NO:32);
Example 30: (Aib$^{2, 28}$, A6c$^7$, Nle$^{14}$)hGIP(1-42)-OH (SEQ ID NO:33);
Example 31: (Aib$^2$, A6c$^7$, Nle$^{14}$)hGIP(1-30)-NH$_2$ (SEQ ID NO:34);
Example 32: (Aib$^2$, A5c$^7$, Nle$^{14}$)hGIP(1-30)-NH$_2$ (SEQ ID NO:35);
Example 33: (Aib$^{2, 11}$, Nle$^{14}$)hGIP(1-30)-NH$_2$ (SEQ ID NO:36);
Example 34: (A5c$^{2, 7}$, Nle$^{14}$)hGIP(1-30)-NH$_2$ (SEQ ID NO:37);
Example 35: (Aib$^2$, A5c$^{7, 14}$)hGIP(1-30)-NH$_2$ (SEQ ID NO:38);
Example 36: (A6c$^{2, 7}$, Nle$^{14}$)hGIP(1-30)-NH$_2$ (SEQ ID NO:39);
Example 37: (Aib$^2$, A6c$^{7, 17}$, Nle$^{14}$)hGIP(1-42)-OH (SEQ ID NO:40);
Example 38: (Aib$^{2, 11}$, A6c$^{14}$)hGIP(1-30)-NH$_2$ (SEQ ID NO:41);
Example 39: (Aib$^2$, A6c$^{7, 14}$)hGIP(1-30)-NH$_2$ (SEQ ID NO:42);
Example 40: (A5c$^2$, Nle$^{14}$)hGIP(1-42)-OH (SEQ ID NO:43);
Example 41: (Aib$^{2, 11}$, A6c$^{14}$)hGIP(1-42)-OH (SEQ ID NO:44);
Example 42: (Aib$^2$, A6c$^{14}$)hGIP(1-42)-OH (SEQ ID NO:45);
Example 43: (Aib$^2$, A6c$^7$)hGIP(1-42)-OH (SEQ ID NO:46);
Example 44: (Aib$^2$, A5c$^7$, A6c$^{14}$)hGIP(1-42)-OH (SEQ ID NO:47);
Example 45: (Aib$^{2, 11}$, Nle$^{14}$)hGIP(1-42)-OH (SEQ ID NO:48);
Example 46: (Aib$^2$, A5c$^{11}$)hGIP(1-30)-NH$_2$ (SEQ ID NO:49);
Example 47: (Aib$^{2, 13}$)hGIP(1-30)-NH$_2$ (SEQ ID NO:50);
Example 48: (Aib$^2$, A5c$^{11}$, A6c$^{14}$)hGIP(1-30)-NH$_2$ (SEQ ID NO:51);
Example 49: (Aib$^{2, 13}$, Nle$^{14}$)hGIP(1-30)-NH$_2$ (SEQ ID NO:52);
Example 50: (Aib$^2$, A5c$^{11}$, Nle$^{14}$)hGIP(1-30)-NH$_2$ (SEQ ID NO:53);
Example 51: (Aib$^2$, A6c$^{7, 14}$)hGIP(1-42)-OH (SEQ ID NO:54);
Example 52: (Aib$^2$, A6c$^7$)hGIP(1-30)-NH$_2$ (SEQ ID NO:55);
Example 53: (Aib$^2$, A5c$^{11}$)hGIP(1-42)-OH (SEQ ID NO:56);
Example 54: (Aib$^2$, A5c$^{11}$, Nle$^{14}$)hGIP(1-42)-OH (SEQ ID NO:57);
Example 55: (Aib$^2$, A6c$^7$, Nle$^{14}$)hGIP(1-42)-OH (SEQ ID NO:58);
Example 56: (A5c$^{2, 7}$, A6c$^{14}$)hGIP(1-42)-OH (SEQ ID NO:59);
Example 57: (Aib$^{2, 13}$, Nle$^{14}$)hGIP(1-42)-OH (SEQ ID NO:60);
Example 58: (Aib$^2$, A5c$^7$, Nle$^{14}$)hGIP(1-42)-OH (SEQ ID NO:61);

Example 59: (Aib², A5c⁷,¹⁴)hGIP(1-42)-OH (SEQ ID NO:62);
Example 60: (Aib²,¹³)hGIP(1-42)-OH (SEQ ID NO:63);
Example 61: (Aib², A5c¹¹, A6c¹⁴)hGIP(1-42)-OH (SEQ ID NO:64);
Example 62: (Pro³, Aib¹³, Nle¹⁴)hGIP(1-42)-OH (SEQ ID NO:65);
Example 63: (hPro³, Aib¹³, Nle¹⁴)hGIP(1-42)-OH (SEQ ID NO:66);
Example 64: (Dhp³, Aib¹³, Nle¹⁴)hGIP(1-42)-OH (SEQ ID NO:67);
Example 65: (hPro³, Aib¹³)hGIP(1-42)-OH (SEQ ID NO:68);
Example 66: (Tic³, Aib¹³)hGIP(1-42)-OH (SEQ ID NO:69);
Example 67: (4Hyp³, Aib¹³)hGIP(1-42)-OH (SEQ ID NO:70);
Example 68: (4Hyp³, Aib¹³, Nle¹⁴)hGIP(1-42)-OH (SEQ ID NO:71);
Example 69: (Tic³, Aib¹³, Nle¹⁴)hGIP(1-42)-OH (SEQ ID NO:72);
Example 70: (3Hyp³, Aib¹³, Nle¹⁴)hGIP(1-42)-OH (SEQ ID NO:73);
Example 71: (Tic³, A6c¹⁴)hGIP(1-42)-OH (SEQ ID NO:74);
Example 72: (hPro³, A6c¹⁴)hGIP(1-42)-OH (SEQ ID NO:75);
Example 73: [Aib², A6c⁷, Cys(Psu)⁴¹]hGIP(1-42)-OH (SEQ ID NO:76);
Example 74: (hPro³, A5c¹¹)hGIP(1-42)-OH (SEQ ID NO:77);
Example 75: (Pro³, Aib¹³)hGIP(1-42)-OH (SEQ ID NO:78);
Example 76: (Pro³, A5c⁷,¹⁴)hGIP(1-42)-OH (SEQ ID NO:79);
Example 77: (Pro³, A5c¹¹)hGIP(1-42)-OH (SEQ ID NO:80);
Example 78: [Aib², A6c⁷, Cys(Psu)⁴⁰]hGIP(1-42)-OH (SEQ ID NO:81);
Example 79: [Aib², A6c⁷, Cys(Psu)³⁹]hGIP(1-42)-OH (SEQ ID NO:82);
Example 80: [Aib², A6c⁷, Cys(Psu)³⁸]hGIP(1-42)-OH (SEQ ID NO:83);
Example 81: [Aib², A6c⁷, Cys(Psu)³⁶]hGIP(1-42)-OH (SEQ ID NO:84);
Example 82: (Tic³, A5c¹¹)hGIP(1-42)-OH (SEQ ID NO:85);
Example 83: (hPro³, A5c¹¹, A6c¹⁴)hGIP(1-42)-OH (SEQ ID NO:86);
Example 84: (4Hyp³, A6c¹⁴)hGIP(1-42)-OH (SEQ ID NO:87);
Example 85: [Aib², A6c⁷, Cys(Psu)³⁵]hGIP(1-42)-OH (SEQ ID NO:88);
Example 86: [Aib², A6c⁷, Cys(Psu)³⁴]hGIP(1-42)-OH (SEQ ID NO:89);
Example 87: (4Hyp³, A5c¹¹)hGIP(1-42)-OH (SEQ ID NO:90);
Example 88: (4Hyp³, A5c¹¹, A6c¹⁴)hGIP(1-42)-OH (SEQ ID NO:91);
Example 89: (Tic³, A5c¹¹, A6c¹⁴)hGIP(1-42)-OH (SEQ ID NO:92);
Example 90: [Aib², A6c⁷, Cys(Psu)³¹]hGIP(1-42)-OH (SEQ ID NO:93);
Example 91: (Pro³, A6c¹⁴)hGIP(1-42)-OH (SEQ ID NO:94);
Example 92: (Pro³, A5c¹¹, Nle¹⁴)hGIP(1-30)-OH (SEQ ID NO:95);
Example 93: (Aib², A6c⁷, Gln⁴³)hGIP(1-43)-OH (SEQ ID NO:96);
Example 94: [Aib², A6c⁷, Cys(Psu)³²]hGIP(1-42)-OH (SEQ ID NO:97);
Example 95: [Aib², A6c⁷, Cys(Psu)⁴³]hGIP(1-43)-OH (SEQ ID NO:98);
Example 96: (Pro³, A5c¹¹, A6c¹⁴)hGIP(1-30)-NH₂ (SEQ ID NO:99);
Example 97: (Pro³, A6c⁷)hGIP(1-30)-NH₂ (SEQ ID NO:100);
Example 98: (Pro³, A5c¹¹)hGIP(1-30)-NH₂ (SEQ ID NO:101);
Example 99: [Aib², A6c⁷, Cys(Psu)³³]hGIP(1-42)-OH (SEQ ID NO:102);
Example 100: [Aib², A6c⁷, Cys(Psu)³⁷]hGIP(1-42)-OH (SEQ ID NO:103);
Example 101: (4Hppa¹, Aib¹³)hGIP(1-42)-OH (SEQ ID NO:104);
Example 102: (Pro³, A5c¹¹, A6c¹⁴)hGIP(1-42)-OH (SEQ ID NO:105);
Example 103: [Orn¹(N—C(O)—(CH₂)₁₂—CH₃), A6c⁷]hGIP(1-42)-OH (SEQ ID NO:106);
Example 104: (D-Ala², A5c¹¹,⁴⁰)hGIP(1-42)-OH;
Example 105: (D-Ala², A5c¹¹, His⁴³)hGIP(1-43)-OH;
Example 106: (D-Ala², A5c¹¹,⁴¹)hGIP(1-42)-OH;
Example 107: (D-Ala², A6c¹¹,¹⁴,⁴¹)hGIP(1-42)-OH;
Example 108: (Aib²,¹³, Pro³, Nle¹⁴)hGIP(1-30)-NH₂ (SEQ ID NO:107);
Example 109: (Aib², Pro³, A6c⁷)hGIP(1-30)-NH₂ (SEQ ID NO:108);
Example 110: (Aib², Pro³, A5c¹¹)hGIP(1-30)-NH₂ (SEQ ID NO:109);
Example 111: (Aib², Pro³, A5c¹¹, Nle¹⁴)hGIP(1-30)-NH₂ (SEQ ID NO:110);
Example 112: (Aib², Pro³, A5c¹¹, A6c¹⁴)hGIP(1-30)-NH₂ (SEQ ID NO:111);
Example 113: (NMe-Tyr¹, Aib², A5c¹¹, Nle¹⁴)hGIP(1-42)-OH (SEQ ID NO:112);
Example 114: (Gly², A6c¹¹,¹⁴,⁴¹)hGIP(1-42)-OH (SEQ ID NO:113);
Example 115: (Gly², Aib¹³, A5c⁴⁰)hGIP(1-42)-OH (SEQ ID NO:114);
Example 116: (Gly², A5c¹¹,⁴¹)hGIP(1-42)-OH (SEQ ID NO:115);
Example 117: (Gly², A5c¹¹, His⁴³)hGIP(1-43)-OH (SEQ ID NO:116);
Example 118: (Gly², A5c¹¹, Nle¹⁴, His⁴³)hGIP(1-43)-OH (SEQ ID NO:117);
Example 119: (D-Ala², A5c¹¹, Nle¹⁴, His⁴³)hGIP(1-43)-OH;
Example 120: (D-Ala², A5c¹¹,¹⁴, His⁴³)hGIP(1-43)-OH;
Example 121: (D-Ala², A5c¹¹,¹⁴)hGIP(1-30)-NH₂;
Example 122: (D-Ala², A5c¹¹, His³¹)hGIP(1-31)-NH₂; and
Example 123: (Aib², A5c¹¹,¹⁴, His⁴³)hGIP(1-43)-OH (SEQ ID NO:118).

According to another aspect of the present invention, a compound according to the present invention as summarized hereinabove and claimed in the appended claims may further comprise a covalently linked PEG moiety, in which said PEG moiety is covalently linked to the compound via a Cys(maleimide), hCys(maleimide), or Pen(maleimide) linker, to form Cys(succinimide-N-PEG), hCys(succinimide-N-PEG), or Pen(succinimide-N-PEG), wherein "succinimide-N-PEG" is either linear or branched as defined hereinbelow. Such PEG moiety has average molecular weight of from about 2,000 to about 80,000, and preferably such PEG moiety is selected from the group consisting of 5K PEG, 10K PEG, 20K PEG, 30K PEG, 40K PEG, 50K PEG, and 60K PEG, to form Cys(succinimide-N-5K PEG), Cys(succinimide-N-10K PEG), Cys(succinimide-N-20K PEG), Cys(succinimide-N-30K PEG), Cys(succinimide-N-40K PEG), Cys(succinimide-N-50K PEG), Cys(succinimide-N-60K PEG), hCys(succinimide-N-5K PEG), hCys(succinimide-N-10K PEG), hCys(succinimide-N-20K PEG), hCys(succinimide- N-30K PEG), hCys(succinimide-N-40K PEG), hCys(succinimide-N-50K PEG), hCys(succinimide-N-60K PEG), Pen(succinimide-N-5K PEG), Pen(succinimide-N-10K PEG), Pen(succinimide-N-20K PEG), Pen(succinimide-N-30K PEG), Pen(succinimide-N-40K PEG), Pen(succinimide-N-50K PEG), or Pen(succinimide-N-60K PEG).

PEGylation occurs at any one of amino acid residue positions 16, 30, and 31-43, and preferably at any one of amino acid residue positions 32, 33 and 43, whereby Cys(succinimide-N-PEG), hCys(succinimide-N-PEG), or Pen(succinimide-N-PEG) is placed in any one of such amino acid residue positions.

Further, the above formula (I) may be expanded to provide PEGylation sites at positions $A^{44}$-$A^{47}$. The C-terminus of such PEGylated compounds of the present invention may be amidated, e.g., $(Aib^{2, 11})hGIP(1-42)-NH_2$ (SEQ ID NO:119), or it may remain as free acid, e.g., $(Aib^{2, 11})hGIP(1-42)-OH$ (SEQ ID NO:4).

DETAILED DESCRIPTION OF THE INVENTION

The application employs the following commonly understood abbreviations:
Abu: α-aminobutyric acid
Acc: 1-amino-1-cyclo($C_3$-$C_9$)alkyl carboxylic acid
A3c: 1-amino-1-cyclopropanecarboxylic acid
A4c: 1-amino-1-cyclobutanecarboxylic acid
A5c: 1-amino-1-cyclopentanecarboxylic acid
A6c: 1-amino-1-cyclohexanecarboxylic acid
Act: 4-amino-4-carboxytetrahydropyran
Ado: 12-aminododecanoic acid
Aib: α-aminoisobutyric acid
Aic: 2-aminoindan-2-carboxylic acid
Ala or A: alanine
β-Ala: beta-alanine
Amp: 4-amino-phenylalanine;
Apc: 4-amino-4-carboxypiperidine:
Arg or R: arginine
hArg: homoarginine
Asn or N: asparagine
Asp or D: aspartic acid
Aun: 11-aminoundecanoic acid
Ava: 5-aminovaleric acid
Cha: β-cyclohexylalanine
Cys or C: cysteine
Dhp: 3,4-dehydroproline
Dmt: 5,5-dimethylthiazolidine-4-carboxylic acid
Gaba: γ-aminobutyric acid
Gln or Q: glutamine
Glu or E: glutamic acid
Gly or G: glycine
His or H: histidine
4Hppa: 3-(4-hydroxyphenyl)propionic acid
3Hyp: 3-hydroxyproline
4Hyp: 4-hydroxyproline
hPro: homoproline
Ile or I: isoleucine
4Ktp: 4-ketoproline
Leu or L: leucine
Lys or K: lysine
Met or M: methionine
Nle: norleucine
NMe-Tyr: N-methyl-tyrosine
1Nal or 1-Nal: β-(1-naphthyl)alanine
2Nal or 2-Nal: β-(2-naphthyl)alanine
Nle: norleucine
Nva: norvaline
Orn: ornithine
2Pal or 2-Pal: β-(2-pyridinyl)alanine
3Pal or 3-Pal: β-(3-pyridinyl)alanine
4Pal or 4-Pal: β-(4-pyridinyl)alanine
Pen: penicillamine
Phe or F: phenylalanine
(3,4,5F)Phe: 3,4,5-trifluorophenylalanine
(2,3,4,5,6)Phe: 2,3,4,5,6-pentafluorophenylalanine
Pro or P: proline
Psu: N-propylsuccinimide
Ser or S: serine
Taz: β-(4-thiazolyl)alanine
3Thi: β-(3-thienyl)alanine
Thr or T: threonine
Thz: thioproline
Tic: tetrahydroisoquinoline-3-carboxylic acid
Tle: tert-leucine
Trp or W: tryptophan
Tyr or Y: tyrosine
Val or V: valine
Certain other abbreviations used herein are defined as follows:
Acn: acetonitrile
Boc: tert-butyloxycarbonyl
BSA: bovine serum albumin
DCM: dichloromethane
DIPEA: diisopropylethyl amine
DMF: dimethylformamide
ESI: electrospray ionization
Fmoc: 9-fluorenylmethyloxycarbonyl
HBTU: 2-(1H-benzotriazole-1-yl)-1,1,3,3-tetramethyluronium hexafluorophosphate
HOBt: 1-hydroxy-benzotriazole
HPLC: high performance liquid chromatography
IBMX: isobutylmethylxanthine
LC-MS: liquid chromatography-mass spectrometry
Mtt: methyltrityl
NMP: N-methylpyrrolidone
5K PEG: polyethylene glycol, which may include other functional groups or moieties such as a linker, and which is either linear or branched as defined hereinbelow, with an average total molecular weight of about 5,000
10K PEG: polyethylene glycol, which may include other functional groups or moieties such as a linker, and which is either linear or branched as defined hereinbelow, with an average total molecular weight of about 10,000
20K PEG: polyethylene glycol, which may include other functional groups or moieties such as a linker, and which is either linear or branched as defined hereinbelow, with an average total molecular weight of about 20,000
30K PEG: polyethylene glycol, which may include other functional groups or moieties such as a linker, and which is either linear or branched as defined hereinbelow, with an average total molecular weight of about 30,000
40K PEG: polyethylene glycol, which may include other functional groups or moieties such as a linker, and which is either linear or branched as defined hereinbelow, with an average total molecular weight of about 40,000
50K PEG: polyethylene glycol, which may include other functional groups or moieties such as a linker, and which is either linear or branched as defined hereinbelow, with an average total molecular weight of about 50,000
60K PEG: polyethylene glycol, which may include other functional groups or moieties such as a linker, and which is either linear or branched as defined hereinbelow, with an average total molecular weight of about 60,000
tBu: tert-butyl TIS: triisopropylsilane
Trt: trityl
TFA: trifluoro acetic acid
Z: benzyloxycarbonyl
"Cys(succinimide-N-alkyl)" has the structure of:

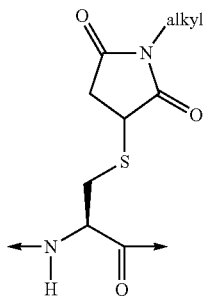

"Cys(Psu)" has the structure of:

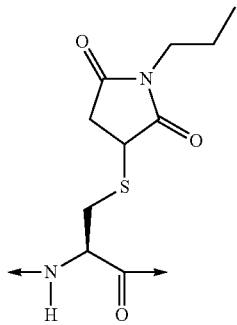

"Orn(N—C(O)—(CH$_2$)$_{12}$—CH$_3$)" has the structure of:

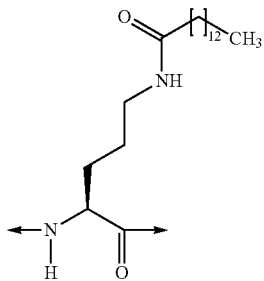

"Cys(succinimide-N—(CH$_2$)x-C(O)—NH—(CH$_2$)y-CH$_3$)" has the structure of:

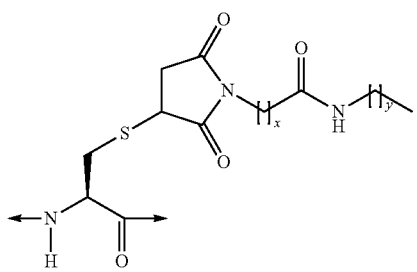

wherein, x=1-30, and y=1-30.

"hCys(succinimide-N—(CH$_2$)$_x$—C(O)—NH—(CH$_2$)$_y$—CH$_3$)" has the structure of:

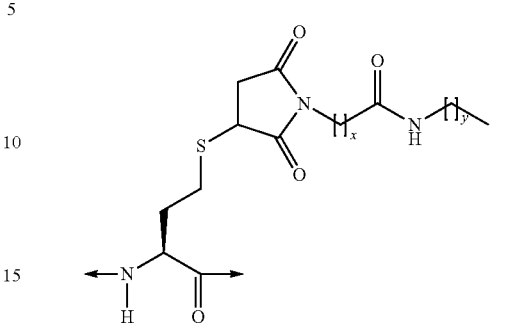

wherein, x=1-30, and y=1-30.

"Pen(succinimide-N—(CH$_2$)$_x$—C(O)—NH—(CH$_2$)$_y$—CH$_3$)" has the structure of:

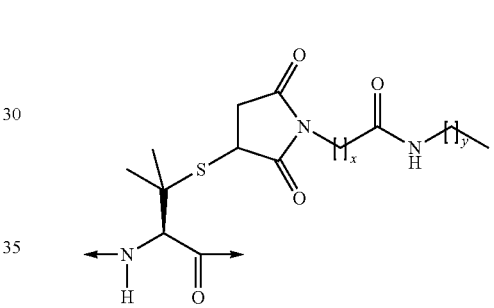

wherein, x=1-30, and y=1-30.

"Cys(succinimide-N—(CH$_2$)$_s$NH—C(O)—(CH$_2$)$_t$—CH$_3$)" has the structure of:

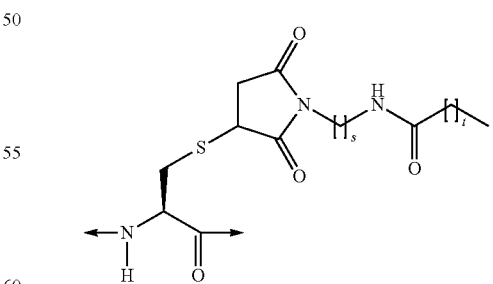

wherein, s=1-30, and t=1-30.

"hCys(succinimide-N—(CH$_2$)$_s$—NH—C(O)—(CH$_2$)$_t$—CH$_3$)" has the structure of:

"Pen(succinimide-N—(CH₂)ₛ—NH—C(O)—(CH₂)ₜ—CH₃)" has the structure of:

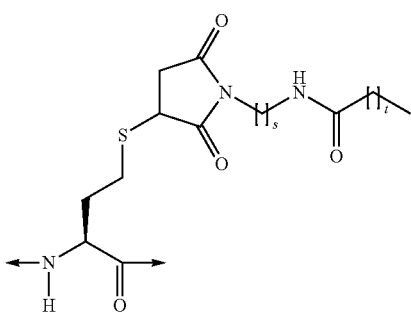

wherein s=1-30, and t=1-30.

"Pen(succinimide-N—(CH₂)ₛ—NH—C(O)—(CH₂)ₜ—CH₃)" has the structure of:

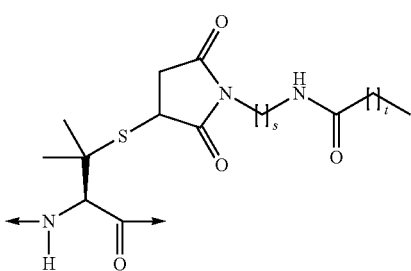

wherein s=1-30, and t=1-30.

"Cys(succinimide-N-PEG)" has the structure of:

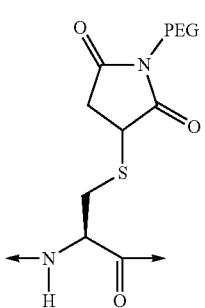

"hCys(succinimide-N-PEG)" has the structure of:

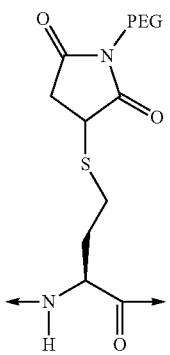

"Pen(succinimide-N-PEG)" has the structure of:

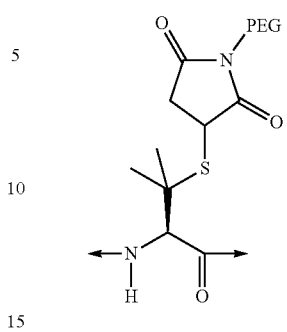

"Cys(succinimide-N—(CH₂)₂—C(O)NH—(CH₂)₃-PEG)" has the structure of:

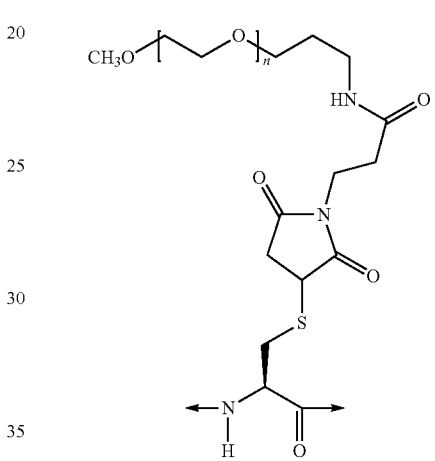

"Cys(succinimide-N—(CH₂)₂—C(O)NH—(CH₂)₃—O—CH₂—CH(PEG)-CH₂-PEG)" has the structure of:

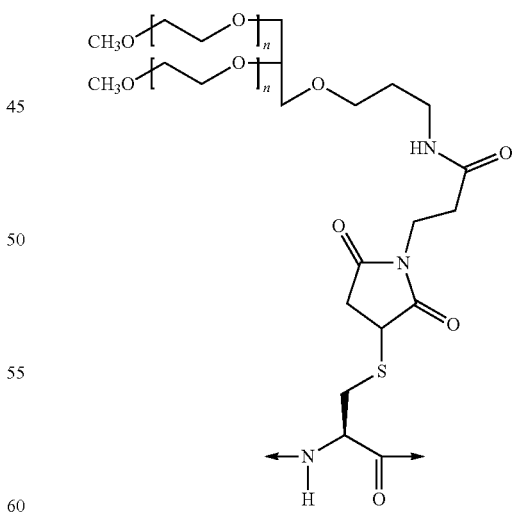

With the exception of the N-terminal amino acid, all abbreviations (e.g., Ala) of amino acids in this disclosure stand for the structure of —NH—C(R)(R')—CO—, wherein R and R' each is, independently, hydrogen or the side chain of an amino acid (e.g., R=CH₃ and R'=H for Ala), or R and R' may be joined to form a ring system. For the N-terminal amino acid, the abbreviation stands for the structure of $(R^2R^3)N$—$C(R)$ $(R')$—CO—, wherein $R^2$ and $R^3$ are as defined in the above formula (I).

The term "$(C_1$-$C_{30})$hydrocarbon moiety" encompasses alkyl, alkenyl and alkynyl, and in the case of alkenyl and alkynyl there are $C_2$-$C_{30}$.

A peptide of this invention is also denoted herein by another format, e.g., $(A5c^2)$hGIP(1-42)-OH (SEQ ID NO:3), with the substituted amino acids from the natural sequence placed between the brackets (e.g., $A5c^2$ for $Ala^2$ in hGIP). The numbers between the parentheses refer to the number of amino acids present in the peptide (e.g., hGIP(1-42)-OH (SEQ ID NO:1) is amino acids 1 through 42 of the peptide sequence for hGIP). The designation "$NH_2$" in hGIP(1-30)-$NH_2$ (SEQ ID NO:2) indicates that the C-terminus of the peptide is amidated; hGIP(1-42) (SEQ ID NO:1) or hGIP(1-42)-OH (SEQ ID NO:1) means that the C-terminus is the free acid.

Human GIP ("hGIP") has the amino acid sequence of:

```
Tyr-Ala-Glu-Gly-Thr-Phe-Ile-Ser-Asp-Tyr-Ser-Ile-Ala-Met-Asp-Lys-Ile-His-Gln-Gln-Asp-Phe-Val-
 1           5              10              15              20
Asn-Trp-Leu-Leu-Ala-Gln-Lys-Gly-Lys-Lys-Asn-Asp-Trp-Lys-His-Asn-Ile-Thr-Gln.(SEQ ID NO: 1)
    25          30              35              40
```

"Acyl" refers to R"—C(O)—, where R" is H, alkyl, substituted alkyl, heteroalkyl, substituted heteroalkyl, alkenyl, substituted alkenyl, aryl, alkylaryl, or substituted alkylaryl.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —$NH_2$, —$NHCH_3$, —$NO_2$, —$C_{1-20}$ alkyl substituted with halogens, —$CF_3$, —$OCH_3$, —$OCF_3$, and —$(CH_2)_{0-20}$—COOH. In different embodiments 1, 2, 3 or 4 substituents are present. The presence of —$(CH_2)_{0-20}$—COOH results in the production of an alkyl acid. Examples of alkyl acids containing, or consisting of, —$(CH_2)_{0-20}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, —OH, —CN, —SH, —$NH_2$, —$NHCH_3$, —$NO_2$, —$C_{1-20}$ alkyl substituted with halogens, —$CF_3$, —$OCH_3$, —$OCF_3$, and —$(CH_2)_{0-20}$—COOH. In different embodiments 1, 2, 3 or 4 substituents are present.

"Alkenyl" refers to a hydrocarbon group made up of two or more carbons wherein one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen, —OH, —CN, —SH, —$NH_2$, —$NHCH_3$, —$NO_2$, —$C_{1-20}$ alkyl substituted with halogens, —$CF_3$, —$OCH_3$, —$OCF_3$, and —$(CH_2)_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —$C_{1-20}$ alkyl, —$C_{1-20}$ alkoxy, halogen, —OH, —CN, —SH, —$NH_2$, —$NO_2$, —$C_{1-20}$ alkyl substituted with halogens, —$CF_3$, —$OCF_3$, and —$(CH_2)_{0-20}$—COOH. In different embodiments the aryl contains 0, 1, 2, 3, or 4 substituents.

"Alkylaryl" refers to an "alkyl" joined to an "aryl".

Synthesis

The peptides of this invention can be prepared by standard solid phase peptide synthesis. See, e.g., Stewart, J. M., et al., 1984, *Solid Phase Synthesis*, Pierce Chemical Co., 2d ed. If $R^1$ is NH—$X^2$—$CH_2$—$CONH_2$, i.e., $Z^0$=$CONH_2$, the synthesis of the peptide starts with Fmoc-HN—$X^2$—$CH_2$—$CONH_2$ which is coupled to Rink amide MBHA resin. If $R^1$ is NH—$X^2$—$CH_2$—COOH, i.e., $Z^0$=COOH, the synthesis of the peptide starts with Fmoc-HN—$X^2$—$CH_2$—COOH which is coupled to Wang resin. For this particular step, 2 molar equivalents of Fmoc-HN—$X^2$—COOH, HBTU and HOBt and 10 molar equivalents of DIPEA are used. The coupling time is about 8 hours.

In the synthesis of a GIP analogue of this invention containing A5c, A6c, and/or Aib, the coupling time is 2 hrs for these residues and the residue immediately following them.

The substituents $R^2$ and $R^3$ of the above generic formula can be attached to the free amine of the N-terminal amino acid $A^1$ by standard methods known in the art. For example, alkyl groups, e.g., $(C_1$-$C_{30})$alkyl, can be attached using reductive alkylation. Hydroxyalkyl groups, e.g., $(C_1$-$C_{30})$hydroxyalkyl, can also be attached using reductive alkylation wherein the free hydroxy group is protected with a tert-butyl ester. Acyl groups, e.g., —C(O)$X^3$, can be attached by coupling the free acid, e.g., —$X^3$COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., 3-fluoro-4-hydroxyphenylacetic acid, then the coupling should be performed with an additional 3 molar equivalents of HOBT.

The following examples describe synthetic methods for making a peptide of this invention, which methods are well-known to those skilled in the art. Other methods are also known to those skilled in the art. The examples are provided for the purpose of illustration and are not meant to limit the scope of the present invention in any manner.

Example 73

[Aib², A6c⁷, Cys(Psu)⁴¹]hGIP(1-42)-OH

Solid-phase peptide synthesis was used to assemble the peptide using microwave-assisted Fmoc Chemistry on a Liberty Peptide Synthesizer (CEM; Matthews, N.C., USA) at the 0.1 mmole scale. Pre-loaded Fmoc-Gln(Trt)-Wang resin (0.59 mmole/g; Novabiochem, San Diego, Calif., USA) was used to generate the C-terminal acid peptide. The resin (0.17 g) was placed in a 50 ml conical tube along with 15 ml of dimethylformamide (DMF) and loaded onto a resin position on the synthesizer. The resin was then quantitatively transferred to the reaction vessel via the automated process. The standard Liberty synthesis protocol for 0.1 mmole scale synthesis was used. This protocol involved deprotecting the N-terminal Fmoc moiety via an initial treatment with 7 ml of 20% piperidine, containing 0.1M N-hydroxybenzotriazole (HOBT), in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration. The resin was then drained and thoroughly washed with DMF several times. The protected amino acid, Fmoc-Thr(tBu)-OH, prepared as 0.2M stock solution in DMF, was then added (2.5 ml, 5 eq.), followed by 1.0 ml of 0.45M (4.5 eq.) HBTU [2-(1H-benzotriazole-1-yl)-1,1,3,3-tetramethyluronium hexafluorophosaphate] in DMF. This was followed by the addition of 0.5 ml of 2M (10 eq.) DIPEA (diisopropylethylamine) in NMP (N-methylpyrrollidinone). The coupling step was performed for 5 minutes using 20 watts of microwave power, a max temperature of 75° C., and the same rate of nitrogen bubbling.

Following the initial coupling step, the reaction vessel was drained to waste and the coupling step repeated. Cycle 2 was then initiated similar to cycle 1. All amino acids were introduced similarly and a double-coupling strategy was employed throughout the entire sequence. Cycles 1-3, 19-20, 25-26, and 30-39 contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 1: Fmoc-Cys(Trt)-OH; Cycle 2: Fmoc-Ile-OH; Cycle 3: Fmoc-Asn(Trt)-OH; Cycle 4: Fmoc-His(Trt)-OH; Cycle 5: Fmoc-Lys(Boc)-OH; Cycle 6: Fmoc-Trp(Boc)-OH; Cycle 7: Fmoc-Asp(OtBu)-OH; Cycle 8: Fmoc-Asn(Trt)-OH; Cycle 9: Fmoc-Lys(Boc)-OH; Cycle 10: Fmoc-Lys(Boc)-OH; Cycle 11: Fmoc-Gly-OH; Cycle 12: Fmoc-Lys(Boc)-OH; Cycle 13: Fmoc-Gln(Trt)-OH; Cycle 14: Fmoc-Ala-OH; Cycle 15: Fmoc-Leu-OH; Cycle 16: Fmoc-Leu-OH; Cycle 17: Fmoc-Trp(Boc)-OH; Cycle 18: Fmoc-Asn(Trt)-OH; Cycle 19: Fmoc-Val-OH; Cycle 20: Fmoc-Phe-OH; Cycle 21: Fmoc-Asp(OtBu)-OH; Cycle 22: Fmoc-Gln(Trt)-OH; Cycle 23: Fmoc-Gln(Trt)-OH; Cycle 24: Fmoc-His(Trt)-OH; Cycle 25: Fmoc-Ile-OH; Cycle 26: Fmoc-Lys(Boc)-OH; Cycle 27: Fmoc-Asp(OtBu)-OH; Cycle 28: Fmoc-Met-OH; Cycle 29: Fmoc-Ala-OH; Cycle 30: Fmoc-Ile-OH; Cycle 31: Fmoc-Tyr(tBu)-Ser(psiMe,Me,Pro)-OH; Cycle 32: Fmoc-Asp(OtBu)-OH; Cycle 33: Fmoc-Ser(tBu)-OH; Cycle 34: Fmoc-A6c-OH; Cycle 35: Fmoc-Phe-OH; Cycle 36: Fmoc-Gly-Thr(psiMe,Me,Pro)-OH; Cycle 37: Fmoc-Glu(OtBu)-OH; Cycle 38: Fmoc-Ala-OH; and Cycle 39: Fmoc-Tyr(tBu)-OH. The coupling protocol for Fmoc-His (Trt)-OH was a slightly modified version of the standard protocol. The microwave power was off for the first 2 minutes, followed by 4 minutes with microwave power on (20 watts; max temperature of 50° C.). Once the peptide backbone was complete, standard piperidine treatment was used to remove the N-terminal Fmoc group. The resin was then thoroughly washed with DMF and then transferred back to the 50 ml conical tube using DMF as the transfer solvent.

The resin was deprotected and cleaved from the resin via treatment with 5 ml of the following reagent: 5% TIS, 2% water, 5% (w/v) dithiothrieitol (DTT), 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted, and the peptide re-suspended in fresh ether. The ether workup was performed a total of 2 times. Following the last ether wash, the peptide was allowed to air dry to remove residual ether. The peptide pellet was resuspended in 8 ml of acetonitrile (Acn) followed by 8 ml of de-ionized water, and allowed to fully dissolve. The peptide solution was then analyzed by mass spectrometry. Mass analysis employing electrospray ionization identified a main product containing a mass of 5011.7 Daltons; corresponding to the desired linear product. The crude product (approximately 500 mg) was analysed by HPLC, employing a 250× 4.6 mm C18 column (Phenomenex; Torrance, Calif., USA) using a gradient of 2-80% acetonitrile (0.1% TFA) over 30 minutes. Analytical HPLC identified a product with 34% purity. The crude peptide was then purified on a preparative HPLC equipped with a C18 reverse phase column using a 10-60% acetonirile (0.1% TFA) over 50 minutes at a 10 ml/min flowrate. The purified peptide was then lyophilized yielding 15 mg of peptide. The linear peptide was then derivatized with N-propylmaleimide (Pma) to generate the propylsuccinimide (Psu) derivative on the Cysteine side chain. The purified linear peptide was brought up in water, adjusted to pH 6.5 with ammonium carbonate, at 5 mg/ml. Five equivalents of Pma was added with constant stirring for 30 seconds. The derivatized peptide solution was then analyzed by mass spectrometry. Mass analysis employing electrospray ionization identified a main product containing a mass of 5150.7 Daltons; corresponding to the desired Psu derivatized product. The product was then re-purified via preparative HPLC using a similar gradient as before. The purified product was analyzed by HPLC for purity (95.10%) and mass spectrometry (5150.9 Daltons) and subsequently lyophilized.

Example 103

[Orn¹(N—C(O)—(CH₂)₁₂—CH₃), A6c⁷]hGIP(1-42)-OH

Solid-phase peptide synthesis was used to assemble the peptide using microwave-assisted Fmoc Chemistry on a Liberty Peptide Synthesizer (CEM; Matthews, N.C., USA) at the 0.1 mmole scale. Pre-loaded Fmoc-Gln(Trt)-Wang resin (0.59 mmole/g; Novabiochem, San Diego, Calif., USA) was used to generate the C-terminal acid peptide. The resin (0.17 g) was placed in a 50 ml conical tube along with 15 ml of dimethylformamide (DMF) and loaded onto a resin position on the synthesizer. The resin was then quantitatively transferred to the reaction vessel via the automated process. The standard Liberty synthesis protocol for 0.1 mmole scale synthesis was used. This protocol involves deprotecting the N-terminal Fmoc moiety via an initial treatment with 7 ml of 20% piperidine, containing 0.1M N-hydroxybenzotriazole (HOBT), in DMF. The initial deprotection step was for 30 seconds with microwave power (45 watts, maximum temperature of 75° C.), and nitrogen bubbling (3 seconds on/7 seconds off). The reaction vessel was then drained and a second piperidine treatment, identical to the first treatment, except that it was for a 3-minute duration. The resin was then drained and thoroughly washed with DMF several times. The protected amino acid, Fmoc-Thr(tBu)-OH, prepared as 0.2M stock solution in DMF, was then added (2.5 ml, 5 eq.), followed by 1.0 ml of 0.45M (4.5 eq.) HBTU [2-(1H-benzotriazole-1-yl)-1,1,3,3-tetramethyluronium hexafluorophosaphate] in DMF. This was followed by the addition of 0.5 ml of 2M (10 eq.) DIPEA (diisopropylethylamine) in NMP (N-methylpyrrollidinone). The coupling step was performed for 5 minutes using 20 watts of microwave power, a max temperature of 75° C., and the same rate of nitrogen bubbling.

Following the initial coupling step the reaction vessel was drained to waste and the coupling step repeated. Cycle 2 was then initiated similar to cycle 1. All amino acids were introduced similarly and a double-coupling strategy was employed throughout the entire sequence. Cycles 1-3, 19-20, 25-26, and 30-39 contained a capping procedure immediately following the coupling step. Capping was performed by adding 7 ml of 0.5M acetic anhydride, containing 0.015M HOBT in NMP, along with 2 ml of the 2M DIPEA solution using a multi-step microwave protocol: 50 watts of power for 30 seconds (65° C. max temperature), followed by 30 seconds of microwave power off, followed by a second round of 30 seconds of microwave power on (50 watts), and then again 30 seconds of no microwave power. The resin was then drained and thoroughly washed with DMF. The following amino acids (Advanced Chemtech, Louisville, Ky., USA) were used: Cycle 1: Fmoc-Thr(tBu)-OH; Cycle 2: Fmoc-Ile-OH; Cycle 3: Fmoc-Asn(Trt)-OH; Cycle 4: Fmoc-His(Trt)-OH; Cycle 5: Fmoc-Lys(Boc)-OH; Cycle 6: Fmoc-Trp(Boc)-OH; Cycle 7: Fmoc-Orn(Mtt)-OH; Cycle 8: Fmoc-Asn(Trt)-OH; Cycle 9: Fmoc-Lys(Boc)-OH; Cycle 10: Fmoc-Lys(Boc)-OH; Cycle 11: Fmoc-Gly-OH; Cycle 12: Fmoc-Lys(Boc)-OH; Cycle 13: Fmoc-Gln(Trt)-OH; Cycle 14: Fmoc-Ala-OH; Cycle 15: Fmoc-Leu-OH; Cycle 16: Fmoc-Leu-OH; Cycle 17: Fmoc-Trp(Boc)-OH; Cycle 18: Fmoc-Asn(Trt)-OH; Cycle 19: Fmoc-Val-OH; Cycle 20: Fmoc-Phe-OH; Cycle 21: Fmoc-Asp(OtBu)-OH; Cycle 22: Fmoc-Gln(Trt)-OH; Cycle 23: Fmoc-Gln(Trt)-OH; Cycle 24: Fmoc-His(Trt)-OH; Cycle 25: Fmoc-Ile-OH; Cycle 26: Fmoc-Lys(Boc)-OH; Cycle 27: Fmoc-Asp(OtBu)-OH; Cycle 28: Fmoc-Met-OH; Cycle 29: Fmoc-Ala-OH; Cycle 30: Fmoc-Ile-OH; Cycle 31: Fmoc-Tyr(tBu)-Ser(psiMe,Me,Pro)-OH; Cycle 32: Fmoc-Asp(OtBu)-OH; Cycle 33: Fmoc-Ser(tBu)-OH; Cycle 34: Fmoc-A6c-OH; Cycle 35: Fmoc-Phe-OH; Cycle 36: Fmoc-Gly-Thr(psiMe,Me,Pro)-OH; Cycle 37: Fmoc-Glu(OtBu)-OH; Cycle 38: Fmoc-Ala-OH; and Cycle 39: Boc-Tyr(tBu)-OH. The coupling protocol for Fmoc-His(Trt)-OH was a slightly modified version of the standard protocol. The microwave power was off for the first 2 minutes, followed by 4 minutes with microwave power on (20 watts; max temperature of 50° C.). Once the peptide backbone was complete, the resin was treated with 12 ml of 1% trifluoroacetic acid (TFA)/5% triisopropylsilane (TIS) in dichloromethane (DCM) for 5 minutes and a $N_2$ sparge rate of 5 seconds on and 10 seconds off. The resin was then drained and again treated with the 1% TFA/5% TIS in DCM solution for 5 minutes. This was performed a total of 7 times to effectively remove the Mtt moiety from the Ornithine side chain. The resin was thoroughly washed with DCM several times, and then treated with the standard piperidine treatment in order to neutralize residual TFA salt on the δN of ornithine. Myristic acid, ($CH_3$—($CH_2$)$_{12}$—COOH; Aldrich, St. Louis, Mo., USA) prepared as a 0.2M solution in DMF, was coupled to the ornithine side chain using the standard amino acid coupling protocol. The resin was then thoroughly washed with DMF and then transferred back to the 50 ml conical tube using DMF as the transfer solvent.

The resin was deprotected and cleaved from the resin via treatment with 5 ml of the following reagent: 5% TIS, 2% water, 5% (w/v) dithiothrieitol (DTT), 88% TFA, and allowed to mix for 3.5 hours. The filtrate was collected into 45 ml of cold anhydrous ethyl ether. The precipitate was pelleted for 10 minutes at 3500 RPM in a refrigerated centrifuge. The ether was decanted, and the peptide re-suspended in fresh ether. The ether workup was performed a total of 2 times. Following the last ether wash the peptide was allowed to air dry to remove residual ether. The peptide pellet was resuspended in 8 ml of acetonitrile (Acn) followed by 8 ml of de-ionized water, and allowed to fully dissolve. The peptide solution was then analyzed by mass spectrometry. Mass analysis employing electrospray ionization identified a main product containing a mass of 5205.1 Daltons; corresponding to the desired linear product. The crude product (approximately 500 mg) was analysed by HPLC, employing a 250× 4.6 mm C18 column (Phenomenex; Torrance, Calif., USA) using a gradient of 2-80% acetonitrile (0.1% TFA) over 30 minutes. Analytical HPLC identified a product with 50% purity. The peptide was then purified on a preparative HPLC equipped with a C18 column using a similar elution gradient. The purified product was re-analyzed by HPLC for purity (95.50%) and mass spectrometry (5156.7 Daltons) and subsequently lyophilized Following lyophillization, 6.2 mg of purified product was obtained representing a 1.2% yield.

Other peptides of the invention can be prepared by a person of ordinary skill in the art using synthetic procedures analogous to those disclosed in the foregoing examples. Physical data for the compounds exemplified herein are given in Table 1.

TABLE 1

| Example Number | Mol. Wt. (Expected) | Mol. Wt. (ESI-MS) | % Purity (HPLC) |
|---|---|---|---|
| 1 | 4995.63 | 4996.5 | 95.67 |
| 2 | 4967.62 | 4968.2 | 97.88 |
| 3 | 4969.55 | 4971.3 | 99.90 |
| 4 | 4981.60 | 4982.9 | 99.90 |
| 5 | 5007.64 | 5007.5 | 96.32 |
| 6 | 4995.59 | 4994.8 | 96.17 |
| 7 | 4995.59 | 4996.6 | 95.84 |
| 8 | 4969.55 | 4968.9 | 93.98 |
| 9 | 4995.63 | 4996.8 | 93.30 |
| 10 | 5025.66 | 5027.0 | 9792 |
| 11 | 3556.04 | 3557.3 | 96.82 |
| 12 | 3543.99 | 3544.6 | 98.93 |
| 13 | 3543.99 | 3545.1 | 97.36 |
| 14 | 3574.06 | 3575.4 | 93.62 |
| 15 | 3530.00 | 3531.1 | 95.36 |
| 16 | 3517.95 | 3525.8 | 99.00 |
| 17 | 3544.03 | 3545.0 | 99.90 |
| 18 | 3516.02 | 3516.3 | 96.03 |
| 19 | 3544.03 | 3544.1 | 99.90 |
| 20 | 3517.95 | 3518.1 | 99.90 |
| 21 | 5005.60 | 5005.6 | 99.90 |
| 22 | 5037.67 | 5037.9 | 94.20 |
| 23 | 4993.62 | 4993.3 | 98.10 |
| 24 | 5019.63 | 5019.4 | 99.00 |
| 25 | 4975.58 | 4975.7 | 99.30 |
| 26 | 5003.59 | 5003.6 | 99.00 |

TABLE 1-continued

| Example Number | Mol. Wt. (Expected) | Mol. Wt. (ESI-MS) | % Purity (HPLC) |
|---|---|---|---|
| 27 | 5003.59 | 5003.8 | 92.90 |
| 28 | 5003.59 | 5004.0 | 95.20 |
| 29 | 5015.64 | 5016.2 | 97.40 |
| 30 | 5005.60 | 5005.4 | 99.00 |
| 31 | 3539.98 | 3540.0 | 98.60 |
| 32 | 3525.95 | 3526.2 | 95.30 |
| 33 | 3525.99 | 3525.8 | 99.90 |
| 34 | 3551.99 | 3552.3 | 99.90 |
| 35 | 3523.93 | 3524.0 | 97.,70 |
| 36 | 3580.04 | 3580.0 | 99.90 |
| 37 | 5003.59 | 5003.5 | 99.90 |
| 38 | 3538.00 | 3538.3 | 99.99 |
| 39 | 3551.99 | 3552.1 | 97.40 |
| 40 | 5005.60 | 5005.5 | 99.00 |
| 41 | 4989.60 | 4989.6 | 99.00 |
| 42 | 4991.57 | 4991.9 | 99.00 |
| 43 | 5009.61 | 5009.5 | 99.00 |
| 44 | 4989.56 | 4989.5 | 99.80 |
| 45 | 4977.59 | 4977.4 | 99.00 |
| 46 | 3570.07 | 3569.8 | 99.00 |
| 47 | 3560.03 | 3557.8 | 99.00 |
| 48 | 5161.42 | 5161.3 | 99.90 |
| 49 | 5017.66 | 5018.0 | 99.90 |
| 50 | 5038.7 | 5038.6 | 99.90 |
| 51 | 5082.53 | 5082.5 | 99.90 |
| 52 | 3558.01 | 2559.8 | 99.00 |
| 53 | 5021.67 | 5021.5 | 94.70 |
| 54 | 5003.63 | 5004.0 | 99.00 |
| 55 | 4991.57 | 4991.3 | 99.00 |
| 56 | 5015.60 | 5015.6 | 98.70 |
| 57 | 4993.59 | 4993.8 | 96.50 |
| 58 | 4977.55 | 4977.8 | 99.00 |
| 59 | 4975.53 | 4975.0 | 99.00 |
| 60 | 5011.63 | 5011.5 | 99.00 |
| 61 | 5015.64 | 5015.9 | 99.00 |
| 62 | 4947.57 | 4948.1 | 99.90 |
| 63 | 4961.59 | 4961.1 | 99.90 |
| 64 | 4961.59 | 4960.6 | 99.90 |
| 65 | 4979.63 | 4980.0 | 99.00 |
| 66 | 5027.68 | 5027.3 | 99.90 |
| 67 | 4981.60 | 4981.3 | 99.70 |
| 68 | 4963.56 | 4963.9 | 99.90 |
| 69 | 5009.64 | 5009.8 | 99.90 |
| 70 | 4963.56 | 4963.3 | 99.90 |
| 71 | 5007.62 | 5007.2 | 98.60 |
| 72 | 4959.57 | 4959.9 | 99.90 |
| 73 | 5150.81 | 5150.9 | 95.10 |
| 74 | 4989.67 | 4989.8 | 98.80 |
| 75 | 4965.60 | 4966.0 | 99.99 |
| 76 | 4929.51 | 4929.6 | 99.00 |
| 77 | 4975.64 | 4975.6 | 97.12 |
| 78 | 5138.75 | 5139.0 | 95.60 |
| 79 | 5137.81 | 5138.1 | 99.90 |
| 80 | 5114.77 | 5114.3 | 99.90 |
| 81 | 5065.70 | 5065.6 | 98.90 |
| 82 | 5037.71 | 5037.9 | 99.90 |
| 83 | 4983.64 | 4983.8 | 99.90 |
| 84 | 4961.55 | 4961.5 | 99.90 |
| 85 | 5136.82 | 5136.6 | 99.90 |
| 86 | 5137.81 | 5137.6 | 99.90 |
| 87 | 4991.64 | 4991.7 | 98.80 |
| 88 | 4985.61 | 4985.2 | 99.90 |
| 89 | 5031.69 | 5031.8 | 99.90 |
| 90 | 5194.86 | 5194.3 | 99.90 |
| 91 | 4945.55 | 4945.0 | 99.90 |
| 92 | 3506.01 | 3505.9 | 99.90 |
| 93 | 5137.74 | 5137.5 | 99.90 |
| 94 | 5123.74 | 5124.0 | 98.30 |
| 95 | 5251.91 | 5252.0 | 98.60 |
| 96 | 3518.02 | 3518.2 | 99.90 |
| 97 | 3511.99 | 3512.0 | 98.80 |
| 98 | 3524.04 | 3523.8 | 99.90 |
| 99 | 5123.74 | 5123.5 | 99.90 |
| 100 | 5123.74 | 5123.5 | 97.90 |
| 101 | 4982.59 | 4982.0 | 99.90 |
| 102 | 4969.62 | 4969.4 | 99.90 |
| 103 | 5156.92 | 5156.7 | 95.50 |
| 104 | 5005.63 | 5005.8 | 97.19 |
| 105 | 5144.78 | 5144.8 | 95.62 |
| 106 | 5017.68 | 5018.4 | 96.00 |
| 107 | 5039.71 | 5040.4 | 99.90 |
| 108 | 3509.99 | 3509.8 | 99.90 |
| 109 | 3526.02 | 3525.7 | 99.00 |
| 110 | 3538.07 | 3538.1 | 99.99 |
| 111 | 3520.03 | 3519.9 | 99.99 |
| 112 | 3532.4 | 3532.0 | 99.90 |
| 113 | 5017.66 | 5018.0 | 99.90 |
| 117 | 5130.8 | 5130.8 | >99 |
| 118 | 5112.7 | 5112.9 | >99 |
| 119 | 5126.7 | 5126.5 | >99 |
| 121 | 3536.0 | 3536.4 | 97.0 |
| 122 | 3693.2 | 3693.5 | 98.2 |
| 123 | 5138.8 | 5138.5 | 99.9 |

Functional Assays

A. In Vitro hGIP Receptor Binding Assay

Membranes for in vitro receptor binding assays were prepared by homogenizing the CHO-K1 clonal cells expressing the human recombinant GIP receptor, with a Brinkman Polytron (setting 6, 15 sec), in ice-cold 50 mM Tris-HCl and then subjected to two centrifugations at 39,000 g for 10 minutes, with a resuspension in fresh buffer in between. For the assay, aliquots of the washed membrane preparations were incubated (100 minutes at 25° C. with 0.05 nM [$^{125}$I]GIP (approximately 2200 Ci/mmol) in 50 mM Tris-HCl, 0.1 mg/ml bacitracin, and 0.1% BSA. The final assay volume was 0.5 ml. The incubations were terminated by rapid filtration through GF/C filters (pre-soaked in 0.5% polyethylenimine) using a Brandel filtration manifold. Each tube and filter were then washed three times with 5-ml aliquots of ice-cold buffer. Specific binding was defined as the total radioligand bound minus that bound in the presence of 1000 nM GIP. In vitro hGIP receptor binding data for the compounds exemplified herein are given in Table 2.

B. Human and Rat Plasma Half-Life Assay

GIP peptide (50 μL 1 mg/ml) was added to 450 μL plasma (human or rat), vertexed briefly and incubated at 37° C. 50 μL was removed at various times, like at 0, 1, 2, 3, 4, 8, 24, 32, 48, 56, 72 hours, mixed with 5 μL formic acid and 150 μL acetonitrile in a microcentrifuge tube, vertexed, and centrifuged for 10 minutes at 10K rpm. The supernatant was transferred to an injection vial and analyzed by LC-MS. The LC-MS system consisted of an API4000 mass spectrometer with an ESI probe. Positive ion mode and full scan detection were used. HPLC separation was carried out on a Luna 3μ C8 (2), 2×30 mm column with a gradient from 90% A to 90% B in 10 minutes at a flow rate of 0.3 ml/min. Buffer A was 1% formic acid in water and buffer B was 1% formic acid acetonitrile. Human and rat plasma half-life data for the compounds exemplified herein are given in Table 2.

TABLE 2

| Example Number | Ki (nM) | Human Plasma T½ (hr) | Rat Plasma T½ (hr) |
|---|---|---|---|
| 1 | 1.20 | >48 | 3.9 |
| 2 | 2.66 | 9.4 | 5.6 |
| 3 | 0.75 | >48 | 5.5 |
| 4 | 4.08 | >48 | 4.8 |
| 5 | 2.26 | >48 | 6.1 |

TABLE 2-continued

| Example Number | Ki (nM) | Human Plasma T½ (hr) | Rat Plasma T½ (hr) |
|---|---|---|---|
| 6 | 0.41 | >48 | 8.6 |
| 7 | 1.65 | 37.1 | 5.3 |
| 8 | 4.98 | >48 | 4.5 |
| 9 | 16.25 | >48 | 9.2 |
| 10 | 80.07 | >48 | 4.0 |
| 11 | 2.05 | 44.4 | >48 |
| 12 | 0.27 | 20.5 | >48 |
| 13 | 0.98 | 35.4 | >48 |
| 14 | 106.63 | 34.8 | 48 |
| 15 | 3.33 | 28.6 | 46.5 |
| 16 | 0.53 | 43.9 | >48 |
| 17 | 15.93 | 17.4 | 55.0 |
| 18 | 5.38 | 11.3 | 44.4 |
| 19 | 0.37 | 27.2 | >48 |
| 20 | 1.84 | 25.4 | 42 |
| 21 | 0.30 | >48 | 12.3 |
| 22 | 6.96 | >48 | 14.2 |
| 23 | 0.87 | >48 | 6.7 |
| 24 | 2.06 | >48 | 24.8 |
| 25 | 1.33 | >48 | 8.4 |
| 26 | 2.54 | N/A | N/A |
| 27 | 120.95 | >48 | 9.3 |
| 28 | 1.09 | >48 | 11.6 |
| 29 | 1.17 | >48 | 7.3 |
| 30 | 1.22 | >48 | 13.4 |
| 31 | 1.04 | 36.5 | 31.4 |
| 32 | 4.90 | >48 | 28.3 |
| 33 | 1.39 | >48 | 34 |
| 34 | 25.80 | >48 | 23 |
| 35 | 2.32 | >48 | 39.4 |
| 36 | 46.97 | 23.7 | 29.2 |
| 37 | 1.06 | >48 | 14.0 |
| 38 | 0.73 | 49.1 | >54 |
| 39 | 1.19 | 42.3 | 43.3 |
| 40 | 15.89 | 7.7 | 4.9 |
| 41 | 0.73 | 15.9 | 13.3 |
| 42 | 0.07 | 10.6 | 6.2 |
| 43 | 0.30 | 8.8 | 7.7 |
| 44 | 0.63 | 9.5 | 7.5 |
| 45 | 0.29 | 18.2 | 11.6 |
| 46 | 0.09 | 12.2 | >54 |
| 47 | 0.33 | 45.3 | 30.8 |
| 48 | 0.15 | >56 | >54 |
| 49 | 0.09 | >56 | 45.0 |
| 50 | 0.16 | 48.1 | >54 |
| 51 | 0.83 | 33.8 | 12.7 |
| 52 | 0.03 | 14.0 | 28.2 |
| 53 | 0.08 | 33.3 | 51.7 |
| 54 | 0.43 | >56 | 44.1 |
| 55 | 0.45 | 8.8 | 11.7 |
| 56 | 34.38 | 16.0 | 9.2 |
| 57 | 0.05 | 30.5 | 13.8 |
| 58 | 0.69 | 37.6 | 16.7 |
| 59 | 0.22 | 24.0 | 13.1 |
| 60 | 0.05 | 26.0 | 10.5 |
| 61 | 0.18 | >48 | 45.3 |
| 62 | 666.95 | 11.4 | 1.4 |
| 63 | 330.11 | 14.2 | 1.4 |
| 64 | 727.37 | 41.3 | 47.5 |
| 65 | N/A | 14.3 | 1.5 |
| 66 | N/A | 19.1 | 8.8 |
| 67 | N/A | >33 | 1.6 |
| 68 | N/A | >48 | 1.9 |
| 69 | N/A | 36.9 | 1.8 |
| 70 | N/A | >33 | 1.5 |
| 71 | N/A | >31 | 4.8 |
| 72 | N/A | 10.7 | 0.45 |
| 73 | 63.57 | N/A | N/A |
| 74 | N/A | 16.3 | 1.3 |
| 75 | N/A | 26.1 | 1.9 |
| 76 | N/A | 55.9 | 1.0 |
| 77 | N/A | 43.3 | 1.5 |
| 78 | 15.97 | 10.1 | 11.2 |
| 79 | 13.78 | N/A | 14.3 |
| 80 | 5.05 | >54 | 5.5 |
| 81 | 635.48 | 8.2 | 6.1 |
| 82 | 503.00 | 9.7 | 10.2 |
| 83 | N/A | 32.4 | 1.1 |
| 84 | 909.50 | 3.3 | 1.9 |
| 85 | 288.33 | 7.3 | 3.5 |
| 86 | 355.54 | 4.2 | 7.0 |
| 87 | N/A | 38.7 | 3.4 |
| 88 | N/A | >48 | 4.4 |
| 89 | 753.50 | >48 | 11.8 |
| 90 | 75.78 | 11.3 | 4.8 |
| 91 | 214.00 | 13.4 | 1.0 |
| 92 | 86.79 | 12.0 | 1.6 |
| 93 | 0.94 | N/A | N/A |
| 94 | 2.59 | N/A | N/A |
| 95 | N/A | N/A | N/A |
| 96 | 870.94 | N/A | N/A |
| 97 | 181.00 | N/A | N/A |
| 98 | 65.85 | N/A | N/A |
| 99 | 1.51 | N/A | N/A |
| 100 | 22.68 | N/A | N/A |
| 101 | 2.25 | 47.5 | 13.4 |
| 102 | 647.50 | 54.1 | 1.7 |
| 103 | 21.47 | 6.8 | >72 |
| 104 | 0.59 | 20.2 | 14.8 |
| 105 | 0.56 | 19.1 | 6.9 |
| 106 | 0.36 | >55 | 9.2 |
| 107 | 6.67 | N/A | N/A |
| 108 | 0.07 | 46.2 | 45.6 |
| 109 | 333.46 | 27.2 | 47.8 |
| 110 | 216.24 | 13.7 | 25.8 |
| 111 | N/A | >54 | >54 |
| 112 | 34.12 | 59.7 | >72 |
| 113 | 0.19 | 61.9 | 27.0 |
| 117 | 0.97 | 25.2 | 10.5 |
| 118 | 0.87 | >42 | 11.2 |
| 119 | 0.66 | 35.7 | 15.4 |
| 121 | 0.46 | N/A | N/A |
| 122 | 0.87 | N/A | N/A |
| 123 | 0.55 | N/A | N/A |

In comparison to the data listed in Table 2, the in vitro hGIP receptor binding data, and human and rat plasma half-life data for [Pro³]hGIP(1-42)-OH, a compound disclosed in PCT publication WO 00/58360, were measured under the same experimental conditions as described hereinabove to be 170.8 nM, and 10.8 hours and 0.8 hours, respectively.

C. Determination of Cyclic AMP Stimulation

1×10⁵ CHO-K1 cells expressing the human recombinant GIP receptor or RIN-5F insulinoma cells were seeded overnight into 24-well cell culture plates (Corning Incorporate, Corning, N.Y., USA). For the assay, the cells were preincubated in 500 µl of Hanks balanced salt solution (Sigma, St. Louis, Mo., USA) with 0.55 mM IBMX (Sigma, St. Louis, Mo., USA) adjusted to pH 7.3 for 10 minutes. GIP or its analogs was then added at a concentration of 100 nM. Following a 30-minute incubation at 37° C., the plates were placed on ice and 500 µl of ice-cold absolute ethanol was added to stop the reaction. The contents of the wells were collected, spun at 2,700 g for 20 minutes at 4° C. to remove cellular debris. The cAMP levels in the supernatants were determined by radioimmunoassay (New England Nuclear, Boston, Mass., USA).

D. Determination of In Vivo Insulin Secretion in Normal Rats

Male Sprague Dawley rats with a body weight of approximately 275-300 g were used as experimental subjects. The day prior to the treatment, right atrial cannulae were implanted via the jugular vein under chlorhydrate. Each cannula was filled with 100 u/ml heparin saline and tied. The rats were fasted for approximately 18 hours prior to dosing with the compound or the vehicle (saline/0.25% BSA). The day of the experiment, aliquots of compound were thawed, brought to room temperature and vortexed thoroughly. A careful check was made for any sign of compound coming out of solution. 10 minutes prior to compound/glucose injection, a 500 μl blood sample was withdrawn and replaced with an equal volume of heparinized saline (10 u/ml). At time 0, a 500 μl blood sample was withdrawn through the cannula. Next, either the vehicle or the appropriate dose of the compound was injected into the cannula and pushed in with the glucose (1 g/kg) or vehicle solution. Finally, 500 μl of volume of heparinized saline (10 u/ml) was used to push in the remaining glucose through the cannula. Additional 500 μl blood samples were withdrawn at 2.5, 5, 10, and 20-minute post-glucose dosing; each immediately followed by a bolus, iv injection of 500 μl heparinized saline (10 u/ml) through the cannula. The plasma was collected from the blood samples by centrifugation, and stored at −20° C. until assay for insulin content. Numerical values of the total insulin secretion, which show the in vivo effects of the compounds of Examples 105, 106, 118, and 119, are summarized in Table 3.

TABLE 3

|  | AUC |
| --- | --- |
| Vehicle/Vehicle | 20.54 |
| Vehicle/Glucose | 4.11 |
| Example 105 | 114.70 |
| Example 106 | 161.73 |
| Example 118 | 88.22 |
| Example 119 | 167.48 |

Administration

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs, (2) 0.25N acetic acid aqueous solution for 0.5 hrs, and (3) a linear gradient (20% to 100% of solution B over 30 minutes) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1\times10^{-7}$ to 200 mg/kg/day, preferably $1\times10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual, or topical routes of administration, and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles include propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. PCT publication WO99/38536 teaches absorbable sustained release compositions of a bioactive agent. PCT publication WO00/04916 teaches a process for making microparticles comprising a therapeutic agent such as a peptide in an oil-in-water process. PCT publication WO00/09166 teaches complexes comprising a therapeutic agent such as a peptide and a phosphorylated polymer. PCT publication WO00/25826 teaches complexes comprising a therapeutic agent such as a peptide and a polymer bearing a non-polymerizable lactone.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

What is claimed is:
1. A compound of formula (I),

$(R^2R^3)\text{-}A^1\text{-}A^2\text{-}A^3\text{-}A^4\text{-}A^5\text{-}A^6\text{-}A^7\text{-}A^8\text{-}A^9\text{-}A^{10}\text{-}A^{11}\text{-}A^{12}\text{-}$
$A^{13}\text{-}A^{14}\text{-}A^{15}\text{-}A^{16}\text{-}A^{17}\text{-}A^{18}\text{-}A^{19}\text{-}A^{20}\text{-}A^{21}\text{-}A^{22}\text{-}$
$A^{23}\text{-}A^{24}\text{-}A^{25}\text{-}A^{26}\text{-}A^{27}\text{-}A^{28}\text{-}A^{29}\text{-}A^{30}\text{-}A^{31}\text{-}A^{32}\text{-}$
$A^{33}\text{-}A^{34}\text{-}A^{35}\text{-}A^{36}\text{-}A^{37}\text{-}A^{38}\text{-}A^{39}\text{-}A^{40}\text{-}A^{41}\text{-}A^{42}\text{-}$
$A^{43}\text{-}R^1$ wherein:
$A^1$ is Tyr;
$A^2$ is Aib;
$A^3$ is Glu;
$A^4$ is Gly, Acc, Aib, or β-Ala;
$A^5$ is Thr, Acc, Aib, or Ser;
$A^6$ is Phe, Acc, Aib, Aic, Cha, 1Nal, 2Nal, 2-Pal, 3-Pal, 4-Pal, $(X^4,X^5,X^6,X^7,X^8)$Phe, or Trp;
$A^7$ is Ile, Abu, Acc, Aib, Ala, Cha, Leu, Nle, Phe, Tle, or Val;
$A^8$ is Ser, Aib, or Thr;
$A^9$ is Asp, Aib, or Glu;
$A^{10}$ is Tyr, Acc, Cha, 1Nal, 2Nal, 2-Pal, 3-Pal, 4-Pal, Phe, or $(X^4,X^5,X^6,X^7,X^8)$Phe;
$A^{11}$ is Ser, Acc, Aib, Nle, or Thr;
$A^{12}$ is Ile, Abu, Acc, Aib, Ala, Cha, Leu, Nle, Phe, Tle, or Val;
$A^{13}$ is Ala, Acc, Aib, β-Ala, D-Ala, Gly, or Ser;
$A^{14}$ is Met, Abu, Acc, Aib, Ala, Cha, Ile, Leu, Nle, Phe, Tle, or Val;
$A^{15}$ is Asp, Aib, or Glu;
$A^{16}$ is Lys, Amp, Apc, Arg, hArg, Orn, HN—CH(($CH_2)_n$—N($R^4R^5$))—C(O), Cys(succinimide-N-alkyl), hCys(succinimide-N-alkyl), Pen(succinimide-N-alkyl), Cys(succinimide-N—($CH_2)_x$—C(O)—NH—($CH_2)_y$—$CH_3$), hCys(succinimide-N—($CH_2)_x$—C(O)—NH—($CH_2)_y$—$CH_3$), Pen(succinimide-N—($CH_2)_x$—C(O)—NH—($CH_2)_y$—$CH_3$), Cys(succinimide-N—($CH_2)_s$—NH—C(O)—($CH_2)_t$—$CH_3$), hCys(succinimide-N—($CH_2)_s$—NH—C(O)—($CH_2)_t$—$CH_3$), or Pen(succinimide-N—($CH_2)_s$—NH—C(O)—($CH_2)_t$—$CH_3$);
$A^{17}$ is Ile, Abu, Acc, Aib, Ala, Cha, Leu, Nle, Phe, Tle, or Val;
$A^{18}$ is His, Amp, Arg, 2-Pal, 3-Pal, 4-Pal, Phe, or Tyr;
$A^{19}$ is Gln, Aib, or Asn;
$A^{20}$ is Gln, Aib, or Asn;
$A^{21}$ is Asp, Aib, or Glu;
$A^{22}$ is Phe, Acc, Aib, Aic, Cha, 1Nal, 2Nal, 2-Pal, 3-Pal, 4-Pal, $(X^4,X^5,X^6,X^7,X^8)$Phe, or Trp;
$A^{23}$ is Val, Abu, Acc, Aib, Ala, Cha, Ile, Leu, Nle, or Tle;
$A^{24}$ is Asn, Aib, or Gln;
$A^{25}$ is Trp, Acc, Aib, 1Nal, 2Nal, 2-Pal, 3-Pal, 4-Pal, Phe, or $(X^4,X^5,X^6,X^7,X^8)$Phe;
$A^{26}$ is Leu, Acc, Aib, Cha, Ile, Nle, Phe, $(X^4,X^5,X^6,X^7,X^8)$Phe, or Tle;
$A^{27}$ is Leu, Acc, Aib, Cha, Ile, Nle, Phe, $(X^4,X^5,X^6,X^7,X^8)$Phe, or Tle;
$A^{28}$ is Ala, Acc, or Aib;
$A^{29}$ is Gln, Aib, Asn, or deleted;
$A^{30}$ is Lys, Amp, Apc, Arg, hArg, Orn, HN—CH(($CH_2)_n$—N($R^4R^5$))—C(O), Cys(succinimide-N-alkyl), hCys(succinimide-N-alkyl), Pen(succinimide-N-alkyl), Cys(succinimide-N—($CH_2)_x$—C(O)—NH—($CH_2)_y$—$CH_3$), hCys(succinimide-N—($CH_2)_x$—C(O)—NH—($CH_2)_y$—$CH_3$), Pen(succinimide-N—($CH_2)_x$—C(O)—NH—($CH_2)_y$—$CH_3$), Cys(succinimide-N—($CH_2)_s$—NH—C(O)—($CH_2)_t$—$CH_3$), hCys(succinimide-N—($CH_2)_s$—NH—C(O)—($CH_2)_t$—$CH_3$), Pen(succinimide-N—($CH_2)_s$—NH—C(O)—($CH_2)_t$—$CH_3$), or deleted;
$A^{31}$ is Gly, Acc, Aib, β-Ala, HN—CH(($CH_2)_n$—N($R^4R^5$))—C(O), Cys(succinimide-N-alkyl), hCys(succinimide-N-alkyl), Pen(succinimide-N-alkyl), Cys(succinimide-N—($CH_2)_x$—C(O)—NH—($CH_2)_y$—$CH_3$), hCys(succinimide-N—($CH_2)_x$—C(O)—NH—($CH_2)_y$—$CH_3$), Pen(succinimide-N—($CH_2)_x$—C(O)—NH—($CH_2)_y$—$CH_3$), Cys(succinimide-N—($CH_2)_s$—NH—C(O)—($CH_2)_t$—$CH_3$), hCys(succinimide-N—($CH_2)_s$—NH—C(O)—($CH_2)_t$—$CH_3$), His, Pen(succinimide-N—($CH_2)_s$—NH—C(O)—($CH_2)_t$—$CH_3$), or deleted;
$A^{32}$ is Lys, Amp, Apc, Arg, hArg, Orn, HN—CH(($CH_2)_n$—N($R^4R^5$))—C(O), Cys(succinimide-N-alkyl), hCys(succinimide-N-alkyl), Pen(succinimide-N-alkyl), Cys(succinimide-N—($CH_2)_x$—C(O)—NH—($CH_2)_y$—$CH_3$), hCys(succinimide-N—($CH_2)_x$—C(O)—NH—($CH_2)_y$—$CH_3$), Pen(succinimide-N—($CH_2)_x$—C(O)—NH—($CH_2)_y$—$CH_3$), Cys(succinimide-N—($CH_2)_s$—NH—C(O)—($CH_2)_t$—$CH_3$), hCys(succinimide-N—($CH_2)_s$—NH—C(O)—($CH_2)_t$—$CH_3$), Pen(succinimide-N—($CH_2)_s$—NH—C(O)—($CH_2)_t$—$CH_3$), or deleted;
$A^{33}$ is Lys, Amp, Apc, Arg, hArg, Orn, HN—CH(($CH_2)_n$—N($R^4R^5$))—C(O), Cys(succinimide-N-alkyl), hCys(succinimide-N-alkyl), Cys(succinimide-N—($CH_2)_x$—C(O)—NH—($CH_2)_y$—$CH_3$), hCys(succinimide-N—($CH_2)_x$—C(O)—NH—($CH_2)_y$—$CH_3$), Pen(succinimide-N—($CH_2)_x$—C(O)—NH—($CH_2)_y$—$CH_3$), Cys(succinimide-N—($CH_2)_s$—NH—C(O)—($CH_2)_t$—$CH_3$), hCys(succinimide-N—

(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{34}$ is Asn, Aib, Gln, Ser, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{35}$ is Asp, Aib, Glu, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{36}$ is Trp, Acc, Aib, 1Nal, 2Nal, 2-Pal, 3-Pal, 4-Pal, Phe, (X$^4$,X$^5$,X$^6$,X$^7$,X$^8$)Phe, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{37}$ is Lys, Amp, Apc, Arg, hArg, Orn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{38}$ is His, Amp, 2-Pal, 3-Pal, 4-Pal, Phe, Tyr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{39}$ is Asn, Aib, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{40}$ is Ile, Acc, Aib, Ser, Thr, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{41}$ is Thr, Acc, Aib, Asn, Gln, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

A$^{42}$ is Gln, Acc, Aib, Asn, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_t$—NH—C(O)—(CH$_2$)$_t$—CH$_3$), or deleted;

A$^{43}$ is Acc, Aib, Ala, Asp, Gln, His, Phe, Thr, Trp, HN—CH((CH$_2$)$_n$—N(R$^4$R$^5$))—C(O), Cys(succinimide-N-alkyl), hCys(succinimide-N-alkyl), Pen(succinimide-N-alkyl), Cys(succinimide-N—(CH$_2$)$_x$—C(O)—NH—(CH$_2$)$_y$—CH$_3$), hCys(succinimide-N—(CH$_2$)$_x$—C(O)—NH—(CH$_2$)$_y$—CH$_3$), Pen(succinimide-N—(CH$_2$)$_x$—C(O)—NH—(CH$_2$)$_y$—CH$_3$), Cys(succinimide-N—(CH$_2$)$_s$—NH—C(O)—(CH$_2$)$_t$—CH$_3$), hCys(succinimide-N—(CH$_2$)$_s$—NH—C(O)—(CH$_2$)$_t$—CH$_3$), Pen(succinimide-N—(CH$_2$)$_s$—NH—C(O)—(CH$_2$)$_t$—CH$_3$), or deleted;

R$^1$ is OH, NH$_2$, (C$_1$-C$_{30}$)alkoxy, or NH—X$^2$—CH$_2$—Z$^0$, wherein X$^2$ is a (C$_0$-C$_{30}$) hydrocarbon moiety and Z$^0$ is H, OH, CO$_2$H, or CONH$_2$;

each of R$^2$, R$^3$, R$^4$ and R$^5$ is independently selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, and substituted aryl(C$_1$-C$_{30}$)acyl; provided that when R$^2$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl; further provided that when R$^4$ is (C$_1$-C$_{30}$)acyl, aryl(C$_1$-C$_{30}$)acyl, substituted (C$_1$-C$_{30}$)acyl, or substituted aryl(C$_1$-C$_{30}$)acyl, then R$^5$ is H, (C$_1$-C$_{30}$)alkyl, (C$_1$-C$_{30}$)heteroalkyl, (C$_2$-C$_{30}$)alkenyl, (C$_2$-C$_{30}$)alkynyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl, or substituted aryl(C$_1$-C$_{30}$)alkyl;

n is, independently for each occurrence, an integer from 1 to 5 inclusive;

s, t, x and y each is, independently for each occurrence, an integer from 1 to 30 inclusive;

$X^4$, $X^5$, $X^6$, $X^7$ and $X^8$ each is, independently for each occurrence, H, F, Cl, Br, I, $(C_{1-10})$alkyl, substituted $(C_{1-10})$alkyl, aryl, substituted aryl, OH, $NH_2$, $NO_2$, or CN;

provided that at least one amino acid residue at positions 4-43 is not the amino acid residue of the corresponding position in native hGIP; and optionally further comprising a covalently linked PEG moiety;

or a pharmaceutically acceptable salt thereof.

2. A compound according to claim 1, wherein:
$A^4$ is Gly or Aib;
$A^5$ is Thr, A5c, or Aib;
$A^6$ is Phe or A6c;
$A^7$ is Ile, A5c, A6c, or Aib;
$A^8$ is Ser or Aib;
$A^9$ is Asp or Aib;
$A^{10}$ is Tyr;
$A^{11}$ is Ser, A5c, A6c, Aib, or Nle;
$A^{12}$ is Ile, A5c, or Aib;
$A^{13}$ is Ala or Aib;
$A^{14}$ is Met, A5c, A6c, or Nle;
$A^{15}$ is Asp;
$A^{16}$ is Lys;
$A^{17}$ is Ile or A6c;
$A^{18}$ is His;
$A^{19}$ is Gln;
$A^{20}$ is Gln;
$A^{21}$ is Asp;
$A^{22}$ is Phe;
$A^{23}$ is Val;
$A^{24}$ is Asn;
$A^{25}$ is Trp;
$A^{26}$ is Leu or A6c;
$A^{27}$ is Leu or A6c;
$A^{28}$ is Ala or Aib;
$A^{29}$ is Gln;
$A^{30}$ is Lys;
$A^{31}$ is Gly, Aib, Cys(Psu), His, or deleted;
$A^{32}$ is Lys, Cys(Psu), or deleted;
$A^{33}$ is Lys, Cys(Psu), or deleted;
$A^{34}$ is Asn, Cys(Psu), or deleted;
$A^{35}$ is Asp, Cys(Psu), or deleted;
$A^{36}$ is Trp, Cys(Psu), or deleted;
$A^{37}$ is Lys, Cys(Psu), or deleted;
$A^{38}$ is His, Cys(Psu), or deleted;
$A^{39}$ is Asn, Cys(Psu), or deleted;
$A^{40}$ is Ile, A5c, A6c, Cys(Psu), or deleted;
$A^{41}$ is Thr, A5c, A6c, Aib, Cys(Psu), or deleted;
$A^{42}$ is Gln or deleted;
$A^{43}$ is Cys(Psu), Gln, His, or deleted;

or a pharmaceutically acceptable salt thereof.

3. A compound according to claim 2, wherein said compound is:

$(Aib^{2,\ 11})hGIP(1-42)-OH$; (SEQ ID NO: 4)

$(Aib^{2,\ 9})hGIP(1-42)-OH$; (SEQ ID NO: 5)

$(Aib^{2,\ 7})hGIP(1-42)-OH$; (SEQ ID NO: 6)

$(Aib^{2,\ 5})hGIP(1-42)-OH$; (SEQ ID NO: 7)

$(Aib^{2},\ A5c^{5})hGIP(1-42)-OH$; (SEQ ID NO: 8)

$(Aib^{2},\ A5c^{7})hGIP(1-42)-OH$; (SEQ ID NO: 9)

$(Aib^{2},\ A5c^{12})hGIP(1-42)-OH$; (SEQ ID NO: 10)

$(Aib^{2,\ 12})hGIP(1-42)-OH$; (SEQ ID NO: 11)

$(Aib^{2,\ 8})hGIP(1-42)-OH$; (SEQ ID NO: 12)

$(Aib^{2,\ 4})hGIP(1-42)-OH$; (SEQ ID NO: 13)

$(Aib^{2},\ A5c^{5})hGIP(1-30)-NH_2$; (SEQ ID NO: 14)

$(Aib^{2},\ A5c^{7})hGIP(1-30)-NH_2$; (SEQ ID NO: 15)

$(Aib^{2},\ A5c^{12})hGIP(1-30)-NH_2$; (SEQ ID NO: 16)

$(Aib^{2,\ 4})hGIP(1-30)-NH_2$; (SEQ ID NO: 17)

$(Aib^{2,\ 5})hGIP(1-30)-NH_2$; (SEQ ID NO: 18)

$(Aib^{2,\ 7})hGIP(1-30)-NH_2$; (SEQ ID NO: 19)

$(Aib^{2,\ 8})hGIP(1-30)-NH_2$; (SEQ ID NO: 20)

$(Aib^{2,\ 9})hGIP(1-30)-NH_2$; (SEQ ID NO: 21)

$(Aib^{2,\ 11})hGIP(1-30)-NH_2$; (SEQ ID NO: 22)

$(Aib^{2,\ 12})hGIP(1-30)-NH_2$; (SEQ ID NO: 23)

$(Aib^{2,\ 13},\ A6c^{7},\ Nle^{14})hGIP(1-42)-OH$; (SEQ ID NO: 24)

$(Aib^{2,\ 31},\ A6c^{7})hGIP(1-42)-OH$; (SEQ ID NO: 25)

$(Aib^{2,\ 41},\ A6c^{7})hGIP(1-42)-OH$; (SEQ ID NO: 26)

$(Aib^{2,\ 31},\ A6c^{7},\ Nle^{14})hGIP(1-42)-OH$; (SEQ ID NO: 27)

$(Aib^{2,\ 41},\ A6c^{7},\ Nle^{14})hGIP(1-42)-OH$; (SEQ ID NO: 28)

$(Aib^{2},\ A6c^{7,\ 26},\ Nle^{14})hGIP(1-42)-OH$; (SEQ ID NO: 29)

$(Aib^{2},\ A6c^{7,\ 27},\ Nle^{14})hGIP(1-42)-OH$; (SEQ ID NO: 30)

$(Aib^{2},\ A6c^{7,\ 40},\ Nle^{14})hGIP(1-42)-OH$; (SEQ ID NO: 31)

$(Aib^{2},\ A6c^{7,\ 41},\ Nle^{14})hGIP(1-42)-OH$; (SEQ ID NO: 32)

$(Aib^{2,\ 28},\ A6c^{7},\ Nle^{14})hGIP(1-42)-OH$; (SEQ ID NO: 33)

-continued (Aib², A6c⁷, Nle¹⁴)hGIP(1-30)-NH₂;  (SEQ ID NO: 34)

(Aib², A5c⁷, Nle¹⁴)hGIP(1-30)-NH₂;  (SEQ ID NO: 35)

(Aib²,¹¹, Nle¹⁴)hGIP(1-30)-NH₂;  (SEQ ID NO: 36)

(A6c²,⁷, Nle¹⁴)hGIP(1-30)-NH₂;  (SEQ ID NO: 39)

(Aib², A6c⁷,¹⁷, Nle¹⁴)hGIP(1-42)-OH;  (SEQ ID NO: 40)

(Aib²,¹¹, A6c¹⁴)hGIP(1-30)-NH₂;  (SEQ ID NO: 41)

(Aib², A6c⁷,¹⁴)hGIP(1-30)-NH₂;  (SEQ ID NO: 42)

(Aib²,¹¹, A6c¹⁴)hGIP(1-42)-OH;  (SEQ ID NO: 44)

(Aib², A6c¹⁴)hGIP(1-42)-OH;  (SEQ ID NO: 45)

(Aib², A6c⁷)hGIP(1-42)-OH;  (SEQ ID NO: 46)

(Aib², A5c⁷, A6c¹⁴)hGIP(1-42)-OH;  (SEQ ID NO: 47)

(Aib²,¹¹, Nle¹⁴)hGIP(1-42)-OH;  (SEQ ID NO: 48)

(Aib², A5c¹¹)hGIP(1-30)-NH₂;  (SEQ ID NO: 49)

(Aib²,¹³)hGIP(1-30)-NH₂;  (SEQ ID NO: 50)

(Aib², A5c¹¹, A6c¹⁴)hGIP(1-30)-NH₂;  (SEQ ID NO: 51)

(Aib²,¹³, Nle¹⁴)hGIP(1-30)-NH₂;  (SEQ ID NO: 52)

(Aib², A5c¹¹, Nle¹⁴)hGIP(1-30)-NH₂;  (SEQ ID NO: 53)

(Aib², A6c⁷,¹⁴)hGIP(1-42)-OH;  (SEQ ID NO: 54)

(Aib², A6c⁷)hGIP(1-30)-NH₂;  (SEQ ID NO: 55)

(Aib², A5c¹¹)hGIP(1-42)-OH;  (SEQ ID NO: 56)

(Aib², A5c¹¹, Nle¹⁴)hGIP(1-42)-OH;  (SEQ ID NO: 57)

(Aib², A6c⁷, Nle¹⁴)hGIP(1-42)-OH;  (SEQ ID NO: 58)

(Aib²,¹³, Nle¹⁴)hGIP(1-42)-OH;  (SEQ ID NO: 60)

(Aib², A5c⁷, Nle¹⁴)hGIP(1-42)-OH;  (SEQ ID NO: 61)

(Aib², A5c⁷,¹⁴)hGIP(1-42)-OH;  (SEQ ID NO: 62)

(Aib²,¹³)hGIP(1-42)-OH;  (SEQ ID NO: 63)

(Aib², A5c¹¹, A6c¹⁴)hGIP(1-42)-OH;  (SEQ ID NO: 64)

-continued

[Aib², A6c⁷, Cys(Psu)⁴¹]hGIP(1-42)-OH;  (SEQ ID NO: 76)

[Aib², A6c⁷, Cys(Psu)⁴⁰]hGIP(1-42)-OH;  (SEQ ID NO: 81)

[Aib², A6c⁷, Cys(Psu)³⁹]hGIP(1-42)-OH;  (SEQ ID NO: 82)

[Aib², A6c⁷, Cys(Psu)³⁸]hGIP(1-42)-OH;  (SEQ ID NO: 83)

[Aib², A6c⁷, Cys(Psu)³⁶]hGIP(1-42)-OH;  (SEQ ID NO: 84)

[Aib², A6c⁷, Cys(Psu)³⁵]hGIP(1-42)-OH;  (SEQ ID NO: 88)

[Aib², A6c⁷, Cys(Psu)³⁴]hGIP(1-42)-OH;  (SEQ ID NO: 89)

[Aib², A6c⁷, Cys(Psu)³¹]hGIP(1-42)-OH;  (SEQ ID NO: 93)

(Aib², A6c⁷, Gln⁴³)hGIP(1-43)-OH;  (SEQ ID NO: 96)

[Aib², A6c⁷, Cys(Psu)³²]hGIP(1-42)-OH;  (SEQ ID NO: 97)

[Aib², A6c⁷, Cys(Psu)⁴³]hGIP(1-43)-OH;  (SEQ ID NO: 98)

[Aib², A6c⁷, Cys(Psu)³³]hGIP(1-42)-OH;  (SEQ ID NO: 102)

[Aib², A6c⁷, Cys(Psu)³⁷]hGIP(1-42)-OH;  (SEQ ID NO: 103)

(NMe-Tyr¹, Aib², A5c¹¹, Nle¹⁴)hGIP(1-42)-OH;  (SEQ ID NO: 112)
or (Aib², A5c¹¹,¹⁴, His⁴³)hGIP(1-43)-OH;  (SEQ ID NO: 118)

or a pharmaceutical salt thereof.

4. A compound according to claim 2, wherein $A^{31}$ to $A^{43}$ are deleted, or a pharmaceutically acceptable salt thereof.

5. A compound consisting essentially of residues 1-30 of SEQ ID NO:1, wherein the sequence comprises an Aib substitution at position 2, and at least one additional amino acid substitution or modification at positions 4-30 that is not the amino acid residue of the corresponding position in native hGIP; or a pharmaceutically acceptable salt thereof.

6. A compound according to claim 5 where at least one of $A^7$, $A^{11}$, $A^{13}$ and $A^{14}$ is not the amino acid residue of the corresponding position in native GIP; or a pharmaceutically acceptable salt thereof.

7. A compound consisting essentially of residues 1-42 of SEQ ID NO:1, wherein the sequence further comprises an Aib substitution at position 2, and at least one additional amino acid substitution or modification at positions 4-42 that is not the amino acid residue of the corresponding position in native hGIP; or a pharmaceutically acceptable salt thereof.

8. A compound according to claim 7, wherein said compound is:
(Aib², A5c¹¹, Nle¹⁴)hGIP(1-42)-OH (SEQ ID NO:57);
or a pharmaceutical salt thereof.

9. A compound according to claim 1, further comprising a covalently linked PEG moiety, or a pharmaceutically acceptable salt thereof, wherein said PEG moiety is selected from the group consisting of 5K PEG, 10K PEG, 20K PEG, 30K PEG, 40K PEG, 50K PEG, and 60K PEG, to form Cys(succinimide-N-5K PEG), Cys(succinimide-N-10K PEG), Cys(succinimide-N-20K PEG), Cys(succinimide-N-30K PEG), Cys(succinimide-N-40K PEG), Cys(succinimide-N-50K PEG), Cys(succinimide-N-60K PEG), hCys(succinimide-N-5K PEG), hCys(succinimide-N-10K PEG), hCys(succinimide-N-20K PEG), hCys(succinimide-N-30K PEG), hCys(succinimide-N-40K PEG), hCys(succinimide-N-50K PEG), hCys(succinimide-N-60K PEG), Pen(succinimide-N-5K PEG), Pen(succinimide-N-10K PEG), Pen(succinimide-N-20K PEG), Pen(succinimide-N-30K PEG), Pen(succinimide-N-40K PEG), Pen(succinimide-N-50K PEG), or Pen(succinimide-N-60K PEG), or a pharmaceutically acceptable salt thereof.

10. A pharmaceutical composition comprising an effective amount of a compound of claim 1.

11. A method for treating type 2 diabetes, comprising the step of administering to a subject in need thereof a therapeutically effective amount of a compound of claim 1.

12. A method of treating diabetes-related disorders, comprising the step of administering to a subject in need thereof a therapeutically effective amount of a compound claim 1, wherein said diabetes-related disorder is selected from the group consisting of hyperglycemia, hyperinsulinemia, impaired glucose tolerance, impaired fasting glucose, dyslipidemia, hypertriglyceridemia, and insulin resistance.

13. A method of stimulating insulin secretion in a subject in need thereof by administering to said subject a therapeutically effective amount of a compound of claim 1.

14. The compound according to claim 2, wherein $A^7$ is A5c or A6c; or a pharmaceutically acceptable salt thereof.

15. The compound according to claim 2, wherein $A^{14}$ is A5c, A6c, or Nle; or a pharmaceutically acceptable salt thereof.

16. The compound according to claim 2, wherein:
$A^7$ is A5c or A6c; and
$A^{14}$ is A5c, A6c, or Nle; or
a pharmaceutically acceptable salt thereof.

* * * * *

UNITED STATES PATENT AND TRADEMARK OFFICE
CERTIFICATE OF CORRECTION

PATENT NO.         : 9,074,014 B2                                    Page 1 of 1
APPLICATION NO.    : 13/057760
DATED              : July 7, 2015
INVENTOR(S)        : Dong It is certified that error appears in the above-identified patent and that said Letters Patent is hereby corrected as shown below:

In the claims:

Claim 1, Column 128, Line 31, "$(CH_2)_t$-NH-C(O)-$(CH_2)_t$-$CH_3$)," should read
-- $(CH_2)_s$-NH-C(O)-$(CH_2)_t$-$CH_3$), or deleted; --

Claim 3, Column 131, Line 10, "(SEQ ID NO: 39)" should read -- (SEQ ID NO: 38) --

Signed and Sealed this
Twenty-second Day of March, 2016

Michelle K. Lee
*Director of the United States Patent and Trademark Office*

```
                          SEQUENCE LISTING

<160> NUMBER OF SEQ ID NOS: 123

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 2

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 3
<211> LENGTH: 42
<212> TYPE: PRT
<213> ORGANISM: Artificial sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid

<400> SEQUENCE: 3

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 4
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
```

```
<220> FEATURE:
<221> NAME/KEY: MISC_FEATURE
<222> LOCATION: (11)..(11)
<223> OTHER INFORMATION: Xaa = alpha-aminoisobutyric acid (Aib)

<400> SEQUENCE: 4

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 5
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = alpha-aminoisobutyric acid (Aib)

<400> SEQUENCE: 5

Tyr Xaa Glu Gly Thr Phe Ile Ser Xaa Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 6
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = alpha-aminoisobutyric acid (Aib)

<400> SEQUENCE: 6

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 7
<211> LENGTH: 42
<212> TYPE: PRT
<213> ORGANISM: Artificial Sequence
<220> FEATURE:
<223> OTHER INFORMATION: Synthetic analog of glucose-dependent
``` insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = alpha-aminoisobutyric acid (Aib)

<400> SEQUENCE: 7

Tyr Xaa Glu Gly Xaa Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 8
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclopentanecarboxylic acid
      (A5c)

<400> SEQUENCE: 8

Tyr Xaa Glu Gly Xaa Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 9
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)

<400> SEQUENCE: 9

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

```
<210> SEQ ID NO 10
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)

<400> SEQUENCE: 10

Tyr Xaa Glu Gly Thr Phe Ile Ser Asp Tyr Ser Xaa Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 11
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = alpha-aminoisobutyric acid (Aib)

<400> SEQUENCE: 11

Tyr Xaa Glu Gly Thr Phe Ile Ser Asp Tyr Ser Xaa Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 12
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)

<400> SEQUENCE: 12

Tyr Xaa Glu Gly Thr Phe Ile Xaa Asp Tyr Ser Ile Ala Met Asp Lys
1               5                   10                  15
```

-continued

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 13
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (4)..(4)
<223> OTHER INFORMATION: Xaa = alpha-aminoisobutyric acid (Aib)

<400> SEQUENCE: 13

Tyr Xaa Glu Xaa Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 14
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 14

Tyr Xaa Glu Gly Xaa Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)

```
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 15

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 16

Tyr Xaa Glu Gly Thr Phe Ile Ser Asp Tyr Ser Xaa Ala Met Asp Lys
1               5                   10                  15

Ile His Gln Gln Asp Phe Val Asn Trp Leu Leu Ala Gln Lys
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (4)..(4)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 17

Tyr Xaa Glu Xaa Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 18
<211> LENGTH: 30
<212> TYPE: PRT
<213> ORGANISM: Artificial Sequence
```

```
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 18

Tyr Xaa Glu Gly Xaa Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 19

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 20

Tyr Xaa Glu Gly Thr Phe Ile Xaa Asp Tyr Ser Ile Ala Met Asp Lys
1               5                   10                  15
```

Ile His Gln Gln Asp Phe Val Asn Trp Leu Leu Ala Gln Lys
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 21

Tyr Xaa Glu Gly Thr Phe Ile Ser Xaa Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 22

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MOD_RES

```
<222> LOCATION: (30)..(30)
<223> OTHER INFORMATION: AMIDATION

<400> SEQUENCE: 23

Tyr Xaa Glu Gly Thr Phe Ile Ser Asp Tyr Ser Xaa Ala Met Asp Lys
1               5                   10                  15

Ile His Gln Gln Asp Phe Val Asn Trp Leu Leu Ala Gln Lys
            20                  25                  30

<210> SEQ ID NO 24
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 24

Tyr Xaa Glu Gly Thr Phe Xaa Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 25
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (31)..(31)
<223> OTHER INFORMATION: Xaa = alpha-aminoisobutyric acid (Aib)

<400> SEQUENCE: 25

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Xaa Lys
            20                  25                  30

Lys Asn Asp Trp Lys His Asn Ile Thr Gln
```

<210> SEQ ID NO 26
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (41)..(41)
<223> OTHER INFORMATION: Xaa = alpha-aminoisobutyric acid (Aib)

<400> SEQUENCE: 26

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 27
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (31)..(31)
<223> OTHER INFORMATION: Xaa = alpha-aminoisobutyric acid (Aib)

<400> SEQUENCE: 27

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Xaa Lys
            20                  25                  30

Lys Asn Asp Trp Lys His Asn Ile Thr Gln
        35                  40

<210> SEQ ID NO 28
<211> LENGTH: 42
<212> TYPE: PRT
<213> ORGANISM: Artificial Sequence
<220> FEATURE:
<223> OTHER INFORMATION: Synthetic analog of glucose-dependent

```
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (41)..(41)
<223> OTHER INFORMATION: Xaa = alpha-aminoisobutyric acid (Aib)

<400> SEQUENCE: 28

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 29
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (26)..(26)
<223> OTHER INFORMATION: Xaa = 1-amino-1-cyclohexanecarboxylic acid
      (A6c)

<400> SEQUENCE: 29

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Xaa Leu Ala Gln Lys Gly Lys
            20                  25                  30

Lys Asn Asp Trp Lys His Asn Ile Thr Gln
        35                  40

<210> SEQ ID NO 30
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
```

```
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (27)..(27)
<223> OTHER INFORMATION: Xaa = 1-amino-1-cyclohexanecarboxylic acid
      (A6c)

<400> SEQUENCE: 30

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Xaa Ala Gln Lys Gly Lys
            20                  25                  30

Lys Asn Asp Trp Lys His Asn Ile Thr Gln
        35                  40

<210> SEQ ID NO 31
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (40)..(40)
<223> OTHER INFORMATION: Xaa = 1-amino-1-cyclohexanecarboxylic acid
      (A6c)

<400> SEQUENCE: 31

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Xaa Thr Gln
        35                  40

<210> SEQ ID NO 32
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
```

```
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (41)..(41)
<223> OTHER INFORMATION: Xaa = 1-amino-1-cyclohexanecarboxylic acid
      (A6c)

<400> SEQUENCE: 32

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 33
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (28)..(28)
<223> OTHER INFORMATION: Xaa = alpha-aminoisobutyric acid (Aib)

<400> SEQUENCE: 33

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Xaa Gln Lys Gly Lys
            20                  25                  30

Lys Asn Asp Trp Lys His Asn Ile Thr Gln
        35                  40

<210> SEQ ID NO 34
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
```

```
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 34

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 35

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 36

Tyr Xaa Glu Gly Thr Phe Ile Ser Asp Tyr Xaa Ile Ala Xaa Asp Lys
1               5                   10                  15
```

Ile His Gln Gln Asp Phe Val Asn Trp Leu Leu Ala Gln Lys
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 37

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 38

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 39
<211> LENGTH: 30
<212> TYPE: PRT
<213> ORGANISM: Artificial Sequence

```
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 39

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 40
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MISC_FEATURE
<222> LOCATION: (17)..(17)
<223> OTHER INFORMATION: Xaa = 1-amino-1-cyclohexanecarboxylic acid
      (A6c)

<400> SEQUENCE: 40

Tyr Xaa Glu Gly Thr Phe Xaa Ser Asp Tyr Ser Ile Ala Xaa Asp Lys
1               5                   10                  15

Xaa His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 41
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
```

```
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 41

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 42

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys
            20                  25                  30

<210> SEQ ID NO 43
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 43

Tyr Xaa Glu Gly Thr Phe Ile Ser Asp Tyr Ser Ile Ala Xaa Asp Lys
```

```
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 44
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 44

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 45
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 45

Tyr Xaa Glu Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 46
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
```

```
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)

<400> SEQUENCE: 46

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 47
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 47

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 48
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 48

Tyr Xaa Glu Gly Thr Phe Ile Ser Asp Tyr Xaa Ile Ala Xaa Asp Lys
1               5                   10                  15
```

```
Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 49
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 49

Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MOD_RES
<222> LOCATION: (30)..(30)
<223> OTHER INFORMATION: AMIDATION

<400> SEQUENCE: 50

Tyr Xaa Glu Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
```

<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 51

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 52

Tyr Xaa Glu Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)

-continued

<223> OTHER INFORMATION: AMIDATION

<400> SEQUENCE: 53

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys
            20                  25                  30

<210> SEQ ID NO 54
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 54

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 55
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 55

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 56
<211> LENGTH: 42
<212> TYPE: PRT
<213> ORGANISM: Artificial Sequence

```
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 56

Tyr Xaa Glu Gly Thr Phe Ile Ser Asp Tyr Xaa Ile Ala Met Asp Lys
 1               5                  10                  15

Ile His Gln Gln Asp Phe Val Asn Trp Leu Leu Ala Gln Lys Gly Lys
                20                  25                  30

Lys Asn Asp Trp Lys His Asn Ile Thr Gln
            35                  40

<210> SEQ ID NO 57
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 57

Tyr Xaa Glu Gly Thr Phe Ile Ser Asp Tyr Xaa Ile Ala Xaa Asp Lys
 1               5                  10                  15

Ile His Gln Gln Asp Phe Val Asn Trp Leu Leu Ala Gln Lys Gly Lys
                20                  25                  30

Lys Asn Asp Trp Lys His Asn Ile Thr Gln
            35                  40

<210> SEQ ID NO 58
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = norleucine (Nle)
```

<400> SEQUENCE: 58

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 59
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 59

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 60
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 60

Tyr Xaa Glu Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

-continued

```
<210> SEQ ID NO 61
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 61

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 62
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)

<400> SEQUENCE: 62

Tyr Xaa Glu Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 63
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
```

```
<221> NAME/KEY: MISC_FEATURE
<222> LOCATION: (13)..(13)
<223> OTHER INFORMATION: Xaa = alpha-aminoisobutyric acid (Aib)

<400> SEQUENCE: 63

Tyr Xaa Glu Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 64
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 64

Tyr Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 65
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 65

Tyr Ala Pro Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 66
```

-continued

```
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 66

Tyr Ala Xaa Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 67
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = 3,4-dehydroproline (Dhp)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 67

Tyr Ala Xaa Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 68
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE
<222> LOCATION: (13)..(13)
<223> OTHER INFORMATION: Xaa = alpha-aminoisobutyric acid (Aib)
```

<400> SEQUENCE: 68

Tyr Ala Xaa Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 69
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = tetrahydroisoquinoline-3-carboxylic acid
      (Tic)
<220> FEATURE:
<221> NAME/KEY: MISC_FEATURE
<222> LOCATION: (13)..(13)
<223> OTHER INFORMATION: Xaa = alpha-aminoisobutyric acid (Aib)

<400> SEQUENCE: 69

Tyr Ala Xaa Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 70
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = 4-hydroxyproline (4Hyp)
<220> FEATURE:
<221> NAME/KEY: MISC_FEATURE
<222> LOCATION: (13)..(13)
<223> OTHER INFORMATION: Xaa = alpha-aminoisobutyric acid (Aib)

<400> SEQUENCE: 70

Tyr Ala Xaa Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 71
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)

```
<223> OTHER INFORMATION: Xaa = 4-hydroxyproline (4Hyp)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 71

Tyr Ala Xaa Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 72
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = tetrahydroisoquinoline-3-carboxylic acid
      (Tic)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 72

Tyr Ala Xaa Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 73
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = 3-hydroxyproline (3Hyp)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 73

Tyr Ala Xaa Gly Thr Phe Ile Ser Asp Tyr Ser Ile Xaa Xaa Asp Lys
1               5                   10                  15
```

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 74
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = tetrahydroisoquinoline-3-carboxylic acid
      (Tic)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 74

Tyr Ala Xaa Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 75
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 75

Tyr Ala Xaa Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 76
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:

```
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (41)..(41)
<223> OTHER INFORMATION: modified with N-propylsuccinimide (Psu)

<400> SEQUENCE: 76

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Cys Gln
        35                  40

<210> SEQ ID NO 77
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 77

Tyr Ala Xaa Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 78
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (13)..(13)
<223> OTHER INFORMATION: Xaa = alpha-aminoisobutyric acid (Aib)

<400> SEQUENCE: 78

Tyr Ala Pro Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 79
<211> LENGTH: 42
<212> TYPE: PRT
<213> ORGANISM: Artificial Sequence
<220> FEATURE:
```

```
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)

<400> SEQUENCE: 79

Tyr Ala Pro Gly Thr Phe Xaa Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 80
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 80

Tyr Ala Pro Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 81
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (40)..(40)
<223> OTHER INFORMATION: modified with N-propylsuccinimide (Psu)

<400> SEQUENCE: 81

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30
```

Lys Asn Asp Trp Lys His Asn Cys Thr Gln
            35                  40

<210> SEQ ID NO 82
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (39)..(39)
<223> OTHER INFORMATION: modified with N-propylsuccinimide (Psu)

<400> SEQUENCE: 82

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Cys Ile Thr Gln
            35                  40

<210> SEQ ID NO 83
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (38)..(38)
<223> OTHER INFORMATION: modified with N-propylsuccinimide (Psu)

<400> SEQUENCE: 83

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys Cys Asn Ile Thr Gln
            35                  40

<210> SEQ ID NO 84
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE

```
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (36)..(36)
<223> OTHER INFORMATION: modified with N-propylsuccinimide (Psu)

<400> SEQUENCE: 84

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Cys Lys His Asn Ile Thr Gln
        35                  40

<210> SEQ ID NO 85
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = tetrahydroisoquinoline-3-carboxylic acid
      (Tic)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 85

Tyr Ala Xaa Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 86
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = homoproline (hPro)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 86

Tyr Ala Xaa Gly Thr Phe Ile Ser Asp Tyr Xaa Ile Ala Xaa Asp Lys
```

```
                 1               5                  10                 15
Ile His Gln Gln Asp Phe Val Asn Trp Leu Leu Ala Gln Lys Gly Lys
                 20                 25                 30

Lys Asn Asp Trp Lys His Asn Ile Thr Gln
         35                  40

<210> SEQ ID NO 87
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = 4-hydroxyproline (4Hyp)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 87

Tyr Ala Xaa Gly Thr Phe Ile Ser Asp Tyr Ser Ile Ala Xaa Asp Lys
1                5                  10                 15

Ile His Gln Gln Asp Phe Val Asn Trp Leu Leu Ala Gln Lys Gly Lys
                 20                 25                 30

Lys Asn Asp Trp Lys His Asn Ile Thr Gln
         35                  40

<210> SEQ ID NO 88
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (35)..(35)
<223> OTHER INFORMATION: modified with N-propylsuccinimide (Psu)

<400> SEQUENCE: 88

Tyr Xaa Glu Gly Thr Phe Xaa Ser Asp Tyr Ser Ile Ala Met Asp Lys
1                5                  10                 15

Ile His Gln Gln Asp Phe Val Asn Trp Leu Leu Ala Gln Lys Gly Lys
                 20                 25                 30

Lys Asn Cys Trp Lys His Asn Ile Thr Gln
         35                  40

<210> SEQ ID NO 89
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
```

```
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (34)..(34)
<223> OTHER INFORMATION: modified with N-propylsuccinimide (Psu)

<400> SEQUENCE: 89

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Cys Asp Trp Lys His Asn Ile Thr Gln
        35                  40

<210> SEQ ID NO 90
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = 4-hydroxyproline (4Hyp)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 90

Tyr Ala Xaa Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 91
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = 4-hydroxyproline (4Hyp)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 91

Tyr Ala Xaa Gly Thr Phe Ile Ser Asp Tyr Xaa Ile Ala Xaa Asp Lys
```

```
                1               5                  10                 15
Ile His Gln Gln Asp Phe Val Asn Trp Leu Leu Ala Gln Lys Gly Lys
                20                  25                 30

Lys Asn Asp Trp Lys His Asn Ile Thr Gln
            35                  40

<210> SEQ ID NO 92
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = tetrahydroisoquinoline-3-carboxylic acid
      (Tic)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 92

Tyr Ala Xaa Gly Thr Phe Ile Ser Asp Tyr Xaa Ile Ala Xaa Asp Lys
1               5                  10                 15

Ile His Gln Gln Asp Phe Val Asn Trp Leu Leu Ala Gln Lys Gly Lys
                20                  25                 30

Lys Asn Asp Trp Lys His Asn Ile Thr Gln
            35                  40

<210> SEQ ID NO 93
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (31)..(31)
<223> OTHER INFORMATION: modified with N-propylsuccinimide (Psu)

<400> SEQUENCE: 93

Tyr Xaa Glu Gly Thr Phe Xaa Ser Asp Tyr Ser Ile Ala Met Asp Lys
1               5                  10                 15

Ile His Gln Gln Asp Phe Val Asn Trp Leu Leu Ala Gln Lys Cys Lys
                20                  25                 30

Lys Asn Asp Trp Lys His Asn Ile Thr Gln
            35                  40

<210> SEQ ID NO 94
<211> LENGTH: 42
```

```
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 94

Tyr Ala Pro Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 95
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 95

Tyr Ala Pro Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 96
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)

<400> SEQUENCE: 96

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Gln
        35                  40
```

```
<210> SEQ ID NO 97
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MOD_RES
<222> LOCATION: (32)..(32)
<223> OTHER INFORMATION: modified with N-propylsuccinimide (Psu)

<400> SEQUENCE: 97

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Cys
            20                  25                  30

Lys Asn Asp Trp Lys His Asn Ile Thr Gln
        35                  40

<210> SEQ ID NO 98
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclopentanecarboxylic acid
      (A5c)
<220> FEATURE:
<221> NAME/KEY: MOD_RES
<222> LOCATION: (43)..(43)
<223> OTHER INFORMATION: modified with N-propylsuccinimide (Psu)

<400> SEQUENCE: 98

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Cys
        35                  40

<210> SEQ ID NO 99
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
```

```
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 99

Tyr Ala Pro Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 100

Tyr Ala Pro Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 101

Tyr Ala Pro Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys
            20                  25                  30

<210> SEQ ID NO 102
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
```

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (33)..(33)
<223> OTHER INFORMATION: modified with N-propylsuccinimide (Psu)

<400> SEQUENCE: 102

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Cys Asn Asp Trp Lys His Asn Ile Thr Gln
        35                  40

<210> SEQ ID NO 103
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (37)..(37)
<223> OTHER INFORMATION: modified with N-propylsuccinimide (Psu)

<400> SEQUENCE: 103

Tyr Xaa Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Cys His Asn Ile Thr Gln
        35                  40

<210> SEQ ID NO 104
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = 3-(4-hydroxyphenyl)propionic acid (4Hppa)
<220> FEATURE:
<221> NAME/KEY: MISC_FEATURE
<222> LOCATION: (13)..(13)
<223> OTHER INFORMATION: Xaa = alpha-aminoisobutyric acid (Aib)

<400> SEQUENCE: 104

Xaa Ala Glu Gly Thr Phe Ile Ser Asp Tyr Ser Ile Xaa Met Asp Lys
1               5                   10                  15
```

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 105
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)

<400> SEQUENCE: 105

Tyr Ala Pro Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 106
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = ornithine (Orn)
<220> FEATURE:
<221> NAME/KEY: MOD_RES
<222> LOCATION: (1)..(1)
<223> OTHER INFORMATION: modified with (N-C(O)-(CH2)12-CH3)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)

<400> SEQUENCE: 106

Xaa Ala Glu Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 107
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:

```
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (13)..(13)
<223> OTHER INFORMATION: Xaa = alpha-aminoisobutyric acid (Aib)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 107

Tyr Xaa Pro Gly Thr Phe Ile Ser Asp Tyr Ser Ile Xaa Xaa Asp Lys
1               5                   10                  15

Ile His Gln Gln Asp Phe Val Asn Trp Leu Leu Ala Gln Lys
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 108

Tyr Xaa Pro Gly Thr Phe Xaa Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MOD_RES
<222> LOCATION: (30)..(30)
<223> OTHER INFORMATION: AMIDATION

<400> SEQUENCE: 109

Tyr Xaa Pro Gly Thr Phe Ile Ser Asp Tyr Xaa Ile Ala Met Asp Lys
```

```
1               5                  10                  15
Ile His Gln Gln Asp Phe Val Asn Trp Leu Leu Ala Gln Lys
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)
<220> FEATURE:
<221> NAME/KEY: MOD_RES
<222> LOCATION: (30)..(30)
<223> OTHER INFORMATION: AMIDATION

<400> SEQUENCE: 110

Tyr Xaa Pro Gly Thr Phe Ile Ser Asp Tyr Xaa Ile Ala Xaa Asp Lys
1               5                  10                  15

Ile His Gln Gln Asp Phe Val Asn Trp Leu Leu Ala Gln Lys
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)
<220> FEATURE:
<221> NAME/KEY: MOD_RES
<222> LOCATION: (30)..(30)
<223> OTHER INFORMATION: AMIDATION

<400> SEQUENCE: 111

Tyr Xaa Pro Gly Thr Phe Ile Ser Asp Tyr Xaa Ile Ala Xaa Asp Lys
1               5                  10                  15

Ile His Gln Gln Asp Phe Val Asn Trp Leu Leu Ala Gln Lys
            20                  25                  30

<210> SEQ ID NO 112
<211> LENGTH: 42
<212> TYPE: PRT
<213> ORGANISM: Artificial Sequence
```

```
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (1)..(1)
<223> OTHER INFORMATION: Xaa = N-methyl-tyrosine (NMe-Tyr)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 112

Xaa Xaa Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 113
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (14)..(14)
<223> OTHER INFORMATION: Xaa = 1-amino-1-cyclohexanecarboxylic acid
      (A6c)
<220> FEATURE:
<221> NAME/KEY: MISC_FEATURE
<222> LOCATION: (41)..(41)
<223> OTHER INFORMATION: Xaa = 1-amino-1-cyclohexanecarboxylic acid
      (A6c)

<400> SEQUENCE: 113

Tyr Gly Glu Gly Thr Phe Ile Ser Asp Tyr Xaa Ile Ala Xaa Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 114
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (13)..(13)
<223> OTHER INFORMATION: Xaa = alpha-aminoisobutyric acid (Aib)
```

```
<220> FEATURE:
<221> NAME/KEY: MISC_FEATURE
<222> LOCATION: (40)..(40)
<223> OTHER INFORMATION: Xaa = 1-amino-1-cyclopentanecarboxylic acid
      (A5c)

<400> SEQUENCE: 114

Tyr Gly Glu Gly Thr Phe Ile Ser Asp Tyr Ser Ile Xaa Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Xaa Thr Gln
        35                  40

<210> SEQ ID NO 115
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (41)..(41)
<223> OTHER INFORMATION: Xaa = 1-amino-1-cyclopentanecarboxylic acid
      (A5c)

<400> SEQUENCE: 115

Tyr Gly Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Xaa Gln
        35                  40

<210> SEQ ID NO 116
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)

<400> SEQUENCE: 116

Tyr Gly Glu Gly Thr Phe Ile Ser Asp Tyr Xaa Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 117
<211> LENGTH: 43
<212> TYPE: PRT
<213> ORGANISM: Artificial Sequence
<220> FEATURE:
<223> OTHER INFORMATION: Synthetic analog of glucose-dependent
```

```
      insulinotropic polypeptide (GIP)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = norleucine (Nle)

<400> SEQUENCE: 117

Tyr Gly Glu Gly Thr Phe Ile Ser Asp Tyr Xaa Ile Ala Xaa Asp Lys
1               5                  10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 118
<211> LENGTH: 43
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = 1-amino-1-cyclopentanecarboxylic acid
      (A5c)
<220> FEATURE:
<221> NAME/KEY: MISC_FEATURE
<222> LOCATION: (14)..(14)
<223> OTHER INFORMATION: Xaa = 1-amino-1-cyclopentanecarboxylic acid
      (A5c)

<400> SEQUENCE: 118

Tyr Xaa Glu Gly Thr Phe Ile Ser Asp Tyr Xaa Ile Ala Xaa Asp Lys
1               5                  10                  15

Ile His Gln Gln Asp Phe Val Asn Trp Leu Leu Ala Gln Lys Gly Lys
            20                  25                  30

Lys Asn Asp Trp Lys His Asn Ile Thr Gln His
        35                  40

<210> SEQ ID NO 119
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (11)..(11)
<223> OTHER INFORMATION: Xaa = alpha-aminoisobutyric acid (Aib)
<220> FEATURE:
<221> NAME/KEY: MOD_RES
<222> LOCATION: (42)..(42)
<223> OTHER INFORMATION: AMIDATION

<400> SEQUENCE: 119
```

```
Tyr Xaa Glu Gly Thr Phe Ile Ser Asp Tyr Xaa Ile Ala Met Asp Lys
1               5                   10                  15

Ile His Gln Gln Asp Phe Val Asn Trp Leu Leu Ala Lys Gly Lys
            20                  25                  30

Lys Asn Asp Trp Lys His Asn Ile Thr Gln
        35                  40

<210> SEQ ID NO 120
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)

<400> SEQUENCE: 120

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 121
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)
<220> FEATURE:
<221> NAME/KEY: MISC_FEATURE
<222> LOCATION: (3)..(3)
<223> OTHER INFORMATION: Xaa = alpha-aminoisobutyric acid (Aib)

<400> SEQUENCE: 121

Tyr Ala Xaa Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 122
<211> LENGTH: 42
<212> TYPE: PRT
<213> ORGANISM: Artificial Sequence
<220> FEATURE:
<223> OTHER INFORMATION: Synthetic analog of glucose-dependent
      insulinotropic polypeptide (GIP)

<400> SEQUENCE: 122

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 123
<211> LENGTH: 42
<212> TYPE: PRT
<213> ORGANISM: Artificial Sequence
<220> FEATURE:
```

<223> OTHER INFORMATION: Synthetic analog of glucose-dependent
      insulinotropic polypeptide (GIP)
<220> FEATURE:
<221> NAME/KEY: MISC_FEATURE
<222> LOCATION: (2)..(2)
<223> OTHER INFORMATION: Xaa = alpha-aminobutyric acid (Abu)

<400> SEQUENCE: 123

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40